(12) United States Patent
Thames et al.

(10) Patent No.: US 6,700,006 B2
(45) Date of Patent: *Mar. 2, 2004

(54) INTERNALLY PLASTICIZING AND CROSSLINKABLE MONOMERS AND APPLICATIONS THEREOF

(75) Inventors: Shelby Freland Thames, Hattiesburg, MS (US); Kamlesh Gopichand Panjnani, Hattiesburg, MS (US); Rajan Hariharan, Norcross, GA (US); Zhiyu Wang, Shaker Heights, OH (US)

(73) Assignee: University of Southern Mississippi, Hattiesburg, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/832,266

(22) Filed: Apr. 10, 2001

(65) Prior Publication Data

US 2001/0031883 A1 Oct. 18, 2001

Related U.S. Application Data

(63) Continuation of application No. 08/773,014, filed on Dec. 24, 1996, now Pat. No. 6,235,916.

(51) Int. Cl.$^7$ ............................................. C07C 59/00
(52) U.S. Cl. .................. 554/219; 106/243; 106/244; 252/182.12; 252/182.14; 252/182.15; 252/182.18; 554/103; 554/108; 554/109; 554/110; 554/113
(58) Field of Search .................. 554/219, 24, 25, 554/30, 103, 108, 109, 110, 113, 114, 213; 106/252, 243, 244; 252/182.12, 182.14, 182.15, 182.16, 182.18

(56) References Cited

U.S. PATENT DOCUMENTS

| | | |
|---|---|---|
| 3,952,032 A | 4/1976 | Vrancken et al. ......... 260/404.8 |
| 4,048,136 A | 9/1977 | Kobayashi et al. ....... 260/42.14 |
| 4,131,580 A | 12/1978 | Emmons et al. ..... 260/29.6 RW |
| 4,141,868 A | 2/1979 | Emmons et al. ......... 260/23 AR |
| 4,144,212 A | 3/1979 | Linder et al. .......... 260/29.7 H |
| 4,226,754 A | 10/1980 | Yun et al. ............. 260/29.6 TA |
| 4,261,872 A | 4/1981 | Emmons et al. ........ 260/22 CB |
| 4,289,675 A | 9/1981 | Krajewski ........... 260/29.6 CM |
| 4,356,128 A | 10/1982 | Rogier ..................... 260/465.6 |
| 4,626,582 A | 12/1986 | Virnig et al. ................ 526/298 |
| 4,745,213 A | 5/1988 | Schlosser et al. ........... 560/217 |
| 4,791,167 A | 12/1988 | Saukaitis ..................... 524/544 |
| 4,826,907 A | 5/1989 | Murao et al. ............... 524/394 |
| 4,906,684 A | 3/1990 | Say ............................. 524/548 |
| 5,243,069 A | 9/1993 | Emmons ..................... 560/224 |
| 5,288,807 A | 2/1994 | Hinz ........................... 525/279 |
| 5,312,889 A | 5/1994 | Frische et al. .............. 528/74.5 |
| 6,001,913 A | 12/1999 | Thames et al. ............. 524/398 |
| 6,174,948 B1 | 1/2001 | Thames et al. ............. 524/398 |

FOREIGN PATENT DOCUMENTS

| | | |
|---|---|---|
| EP | 0 466 409 A1 | 1/1992 |
| IN | 154467 | 7/1980 |
| IN | 153599 | 6/1981 |
| IN | 154647 | 8/1981 |

OTHER PUBLICATIONS

Journal of the American Oil Chemists' Society, Nelson, Jane S. and Applewhite, Thomas H., "Castor–Based Derivatives: Synthesis of Some Acrylate Esters", Sep., 1966, pp. 542–545.

*Primary Examiner*—Judy M. Reddick
(74) *Attorney, Agent, or Firm*—Howrey Simon Arnold & White, LLP

(57) ABSTRACT

Novel compounds derived from traditional semi- drying and non-drying oils featuring internally plasticizing and crosslinkable properties are disclosed and claimed. Preferred embodiments include acrylate or methacrylate esters of hydroxy long-chain olefinic compounds derived from castor oil or lesquerella oil. A process for the preparation of the novel compounds is also disclosed, which involves esterification reaction of ethylenically unsaturated carboxylic acids or its derivatives with substituted hydroxy long-chain olefinic compounds. These compounds are suitable for forming latices, which form films at low minimum film forming temperatures (MFT) ranging from −5 to 10° C. and cure to above ambient glass transition ($T_g$) polymers without the use of traditional organic cosolvents which contribute to environmental pollution via volatile organic compounds (VOCs) emissions. These latices are therefore useful in waterborne coatings, contact and pressure sensitive adhesives, and inks.

4 Claims, No Drawings

INTERNALLY PLASTICIZING AND CROSSLINKABLE MONOMERS AND APPLICATIONS THEREOF

This is a continuation of application Ser. No. 08/773,014 filed Dec. 24, 1996, now U.S. Pat. No. 6,235,916 B1.

BACKGROUND OF THE INVENTION

1. Field of the Invention

This invention relates to new compositions of matter which contain an ethylenically unsaturated carboxylic ester moiety, and are derived from traditional semi-drying and non-drying oils. More particularly, though not exclusively, this invention relates both to novel compositions of acrylate and methacrylate esters of a long-chain olefinic moiety derived from non-drying oils such as castor oil or lesquerella oil and to a process for making these compositions. The invention is also directed to novel waterbome latex compositions formed from these novel acrylate or methacrylate compositions having utility in coatings, adhesives and inks to improve and enhance the general application and performance properties of these formulations.

2. Description of the Prior Art

Recent Congressional enactments have forced coatings manufacturers to develop new coating formulations that contain low VOCs yet feature good performance properties. However, attempts at developing new formulations that contain environmentally acceptable low VOCs have only resulted in formulations with poor performance characteristics which are also economically unattractive.

One problem encountered by the coatings manufacturers is the development of formulations containing low VOC-coalescing aids or plasticizers. For instance, emulsion polymers are currently formulated with coalescing aids or plasticizers in order to form films at and below ambient conditions yet dry to films of sufficient glass transition temperature ($T_g$) to perform adequately at and above room temperature. In general, the ability of emulsion polymers to form or coalesce into film is governed by the minimum film forming temperature (MFT) of the polymer in question, which typically approximates $T_g$ of that polymer. Thus, there is a dilemma, i.e., low MFT polymers are required in order to exhibit coalescence, flow, and surface wetting properties. However, if the polymer remains soft and tacky, the coatings are not usable. Therefore, it is necessary to develop a technology in which coating formulations contain suitable ingredients with an initial low MFT, followed upon application forms nontacky, durable, hard, and water resistant surfaces having a $T_g$ significantly above their MFT.

There are few references in literature which describe low MFT coating compositions which cure to form high $T_g$ films. One such example utilizes a terpolymer binder known as Vinamul 3692, which is used in solventless paints. The terpolymer is formed from ethylene, vinyl acetate, and acrylated ethylene vinyl acetate. Although the physical properties of the paint films are generally good, the latex synthesis involves the use of ethylene in high pressure reactors. Such a manufacturing protocol is not available to most latex manufacturers and is not cost effective.

There have been many other reports that disclose coatings compositions that cure or dry at ambient conditions into durable products. For example, vinylic derivatives of autooxidizable drying oils have been synthesized, which are formulated into crosslinkable emulsion compositions. However, these emulsion compositions still required the use of VOCs for film formation and formulation into usable coatings. Moreover, the polymers possessed other drawbacks, i.e., the free radical polymerizations of vinyl monomers of high iodine number oils are kinetically unfavorable and the products exhibit moderate to marked incompatibility.

Various other coating compositions which cure under ambient conditions are known in the prior art. A few such examples involve curing by a chemical reaction such as epoxide-carboxylic acid reaction, isocyanate-moisture reaction, polyaziridine-carboxylic acid reaction, and activated methylene-unsaturated acrylic reaction.

There are also literature references which disclose derivatives of fatty compounds suitable in the formation of coatings. For example, acryloxymethyl substituted fatty compounds have been claimed to be useful in radiation curable coating formulations and as binders in inks. Acrylate esters of castor oil have also been reported to be potentially useful as binders in coatings and other applications.

However, none of these references discloses use of an internally plasticizing and crosslinkable monomer derived from either a traditional semi-drying or a non-drying oil for the formation of coating formulations. In addition, none of the references discussed above utilizes inexpensive and readily available acrylate or other ethylenically unsaturated esters of long-chain olefinic monomers derived from semi- or non-drying oils to form latex or emulsion compositions. Furthermore, none of the references mentioned above describes latex or emulsion compositions featuring low MFTs that cure to above ambient $T_g$ without the use of any VOCs and yet featuring enhanced properties.

Therefore, it is an object of this invention to provide novel compositions having low VOCs and low odor which are suitable for forming coatings, adhesives, and inks formulations comprising an internally plasticizing and crosslinkable monomer. An additional objective of this invention is to provide a process for the synthesis of the novel latex or emulsion compositions. It is also an objective of this invention to provide novel internally plasticizing and crosslinkable monomers derived (or obtained) from semi- or non-drying oils, and processes for making the same. Yet another objective of this invention is to provide a variety of utilities for these novel compositions. Such utilities include as a binder in coatings, adhesives, and inks formulations featuring enhanced properties yet contributing zero VOCs. The compositions of the present invention have no precedence in the prior art.

Prior Art

The following references are disclosed as background art and for informational purpose.

U.S. Pat. No. 4,626,582 discloses acyloxymethyl fatty compounds which are useful as monomers in the preparation of radiation curable coatings.

U.S. Pat. No. 4,826,907 discloses an acrylic or methacrylic resin emulsion coating composition, and its use.

U.S. Pat. No. 4,906,684 discloses ambient curing coating compositions which are made from aqueous dispersions of copolymers of acetoacetoxyethyl acrylate or methacrylate, glycidyl acrylate or methacrylate, and ethylenically unsaturated polymerizable acid and a different monomer copolymerizable therewith.

Eur. Pat. Appln. No. 466,409 discloses a polymer blend useful as a binder in an aqueous coating composition containing no coalescent.

Indian Pat. No. 153,599 describes a process for preparing novel vinyl monomers from ricinoleic acid and mixed fatty acids of castor oil.

Indian Pat. No. 154,467 describes a process for the preparation of novel acrylic monomers and polymers from castor oil and methyl ricinoleate.

*J. American Oil Chem. Soc.,* (1966) (pp 542–545) describes synthesis of acrylate esters of various hydroxy acid derivatives obtainable from castor oil.

Al of the references described herein are incorporated herein by reference in their entirety.

SUMMARY OF THE INVENTION

Surprisingly, it has now been found that coatings, adhesives and inks having essentially no VOCs can readily be formed from novel latex or emulsion compositions. In addition, the novel compositions of the present invention are comprised of a monomer which features a plasticizing property, and thus serves as an internal plasticizer and subsequently as a crosslinking agent. The monomers suitable for forming the latex or emulsion compositions of this invention are derivatives of semi- or non-drying oils having an ethylenically unsaturated ester of a long-chain olefinic compound. Preferred monomers of this invention are acrylate or methacrylate esters of long-chain olefinic monomers derived (or obtained) from either castor oil or lesquerella oil. The latices formed by this invention have utility in numerous applications such as in coatings, adhesives, and inks formulations.

Accordingly, the present invention provides a composition having low volatile organics content and low odor that is suitable for forming coatings, adhesives, and inks formulations comprising an aqueous dispersion composed of a blended mixture of:

(a) a polymer obtained by the polymerization of:
  (i) an internally plasticizing and crosslinkable monomer derived from a semi- or non-drying oil; and
  (ii) one or more of ethylenically unsaturated monomers copolymerizable therewith;
(b) a drier selected from the group consisting of aliphatic carboxylic acid salts of cobalt, manganese, lead, zirconium, calcium, and mixtures thereof; and
(c) a surface-active agent; wherein the total weight percent of the polymer in said aqueous dispersion is at least from about 5 and not more than about 80 weight percent, wherein the monomers (i) and (ii) are present in the weight ratio ranging from about 1:2 to about 1:99.

In another aspect of the present invention, a process for the formation of a waterborne formulation for coatings, inks or adhesives containing a polymer formed from an ethylenically unsaturated ester of a long-chain olefinic compound derived (or obtained) from a semi- or non-drying oil is also provided.

In further aspects of this invention novel monomers suitable for forming the above mentioned latex or emulsion compositions, and processes for making these monomers are also provided.

DETAILED DESCRIPTION OF THE INVENTION

Surprisingly, it has now been found that coatings, adhesives and inks having essentially no VOCs can readily be formed from novel latex or emulsion compositions. In addition, the novel compositions of the present invention are comprised of a monomer which features a plasticizing property, and thus serves as an internal plasticizer. The monomers suitable for forming the latex or emulsion compositions of this invention are derivatives of semi- or non-drying oils having an ethylenically unsaturated ester of a long-chain olefinic compound. Preferred monomers of this invention are acrylate or methacrylate esters of long-chain olefinic monomers derived (or obtained) from either castor oil or lesquerella oil. The latices formed by this invention have utility in numerous applications such as in coatings, adhesives, and inks formulations.

Accordingly, the present invention provides a composition having low volatile organic content and low odor that is suitable for forming coatings, adhesives, and inks formulations comprising an aqueous dispersion composed of a blended mixture of:

(a) a polymer obtained by the polymerization of:
  (i) an internally plasticizing and crosslinkable monomer derived from a semi- or non-drying oil; and
  (ii) one or more of ethylenically unsaturated monomers copolymerizable therewith;
(b) a drier selected from the group consisting of aliphatic carboxylic acid salts of cobalt, manganese, lead, zirconium, calcium, and mixtures thereof; and
(c) a surface-active agent;
wherein the total weight percent of the polymer in said aqueous dispersion is at least from about 5 and not more than about 80 weight percent, wherein the monomers (i) and (ii) are present in the weight ratio ranging from about 1:2 to about 1:99.

As used herein, the term internally plasticizing monomer is intended to be generic to a class of compounds wherein the monomers of this invention are capable of polymerizing and at the same time act as a plasticizer (i.e., "in-chain" or "internal plasticization") for the polymer formed therefrom. Generally, the coatings formulations contain a volatile organic solvent additive(s) that acts as a plasticizer for the polymeric binder. The role of these volatile organic plasticizers is to reduce the apparent $T_g$ of the polymer thereby permitting the coating to form a useful film at a temperature below the real $T_g$ of the polymer. Thus, by incorporating the internally plasticizing monomers of the present invention, the polymers or copolymers formed in this invention are self plasticized with no subsequent VOC emissions. As a result, the compositions of the present invention which are suitable for forming coatings, adhesives, and inks exhibit lower minimum film forming temperatures (METs) than the corresponding $T_g$'s of the cured compositions.

Additionally, the internally plasticizing monomers of the present invention are also capable of crosslinking during the drying process. The term crosslinking used herein is intended to mean that the monomers of the present invention are capable of bonding to itself, and/or another compound or polymeric chain triggered by a suitable chemical or physical reaction. In a typical coating formulation, for example, the formulation is first applied onto a desired surface and then cured by suitable means during which time the crosslinking of the polymeric binder occurs. Thus, the monomers of the present invention may be crosslinked after forming films from the coating compositions. Curing can be affected by a wide variety of well known techniques in the art.

The internally plasticizing and crosslinkable monomers of the present invention are preferably derived from semi- or non-drying oils. The term derived used herein is intended to mean that the monomers of the present invention are obtained or formed from a wide variety of semi- or non-drying oils. Various chemical and physical modifications of these semi- or non-drying oils may be made to obtain the desirable monomers of the present invention using the methods well known in the art.

Various semi- and non-drying oils may be employed for the formation of the monomers of the present invention. The terms semi- and non-drying oils used herein are defined as those oils which do not show marked increase in viscosity on exposure to air. Generally, oils are classified as drying, semi-drying, or non-drying based on their "iodine value," that is, the number of grams of iodine required to saturate the double bonds of 100 grams of an oil. In accordance with this definition, oils having an iodine value of about 120 to 150 are generally considered to be semi-drying oils, and oils having less than 120 are generally considered to be non-drying oils. Illustrative examples of such semi-drying oils include safflower oil, sunflower oil, soybean oil, and tobaccoseed oil. Illustrative examples of such non-drying oils include cottonseed oil, coconut oil, rapeseed oil, castor oil, and lesquerella oil. A detailed description of the classification of various oils may be found in *"Surface Coatings— Raw Materials and Their Usage,"* Vol., Chapman and Hall, Chapter 4, p-45, (1993), incorporated herein by reference in its entirety.

Accordingly, the preferred internally plasticizing and crosslinkable monomers derived from semi- or non-drying oils of the present invention are substituted ethylenically unsaturated carboxylic acid esters of long-chain olefinic compounds of the formula I:

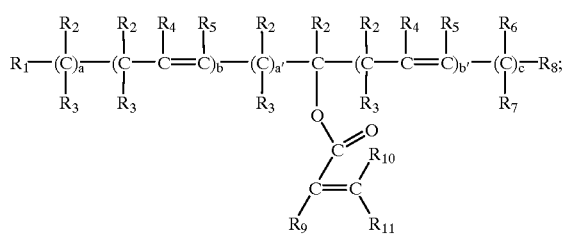

(I)

wherein (a) $R_1$, $R_2$, $R_3$, $R_4$, $R_5$, $R_6$, and $R_7$, are the same or different and are each independently selected from the group consisting of:

hydrogen;

alkoxy group having 1 to 10 carbon atoms;

alkoxyalkyl group having 1 to 10 carbon atoms; and linear or branched alkyl and fluoroalkyl groups having the formula $C_nH_xF_y$, where n is an integer from 1 to 10, x and y are integers from 0 to 2n+1, and the sum of x and y is 2n+1;

(b) $R_8$ is selected from the group consisting of:

—CN;

—COOR;

—CH$_2$OH;

—CH$_2$OR;

—CONR'R"; and

—CH$_2$NR'R";

where (i) R is selected from the group consisting of:

phenyl and substituted phenyl;

tolyl and substituteatolyl;

benzyl and substituted benzyl;

alkoxyalkyl group having 1 to 10 carbon atoms;

hydroxyalkyl group having 1 to 10 carbon atoms;

acyloxyalkyl group having 1 to 10 carbon atoms;

a linear or branched alkenyl group having 2 to 10 carbon atoms;

linear or branched alkyl and fluoroalkyl groups having the formula $C_nH_xF_y$, where n is an integer from 1 to 10, x and y are integers from 0 to 2n+1, and the sum of x and y is 2n+1; and a multifunctional moiety having the structure II or III:

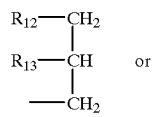

(II)

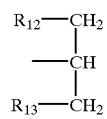

(III)

where $R_{12}$ and $R_{13}$ are the same or different and are independently selected from the group consisting of:

a substituted or unsubstituted, saturated or unsaturated fatty acid chain; acrylic and substituted acrylic;

a linear or branched alkyl or alkenyl carboxylic acid moiety having 2 to 30 carbon atoms; and monoalkyl esters of maleic and fumaric acids, where alkyl group contains 1 to 4 carbon atoms;

(ii) R', and R" are the same or different and are independently selected from the group consisting of:

hydrogen;

phenyl and substituted phenyl;

tolyl and substituted tolyl;

benzyl and substituted benzyl;

alkoxyalkyl group having 1 to 10 carbon atoms;

hydroxyalkyl group having 1 to 10 carbon atoms;

acyloxyalkyl group having 1 to 10 carbon atoms;

a linear or branched alkenyl group having 2 to 10 carbon atoms; and linear or branched alkyl and fluoroalkyl groups having the formula $C_nH_xF_y$, where n is an integer from 1 to 10, x and y are integers from 0 to 2n+1, and the sum of x and y is 2n+1;

(c) $R_9$, $R_{10}$, and $R_{11}$ are the same or different and are independently selected from the group consisting of:

hydrogen;

a carboxylate of the formula —COOR, where R is alkyl group having 1 to 10 carbon atoms, or phenyl and substituted phenyl;

phenyl and substituted phenyl;

tolyl and substituted tolyl;

benzyl and substituted benzyl;

a linear or branched alkenyl group having 2 to 10 carbon atoms; and linear or branched alkyl and fluoroalkyl groups having the formula $C_nH_xF_y$, where n is an integer from 1 to 10, x and y are integers from 0 to 2n+1, and the sum of x and y is 2n+1; and (d) a, a', b, b', and c, are integers, where a and a' have a value of from 0 to 10, b and b' have a value of 0 to 2 with the proviso that sum of b and b' is 1 or 2, and c has a value of from 0 to 20.

In the above definitions and throughout the present specification, alkoxy means straight or branched chain alkoxy having 1 to 10 carbon atoms, and includes, for example, methoxy, ethoxy, n-propoxy, isopropoxy, n-butoxy, isobutoxy, tert-butoxy, pentyloxy, hexyloxy, heptyloxy, octyloxy, nonanyloxy, decanyloxy, 4-methylhexyloxy, 2-propylheptyloxy, and 2-ethyloctyloxy.

Alkoxyalkyl means that the alkoxy moiety and the alkyl moiety each are straight or branched chains having 1 to 10 carbon atoms, and includes, for example, methoxymethyl, ethoxymethyl, propoxymethyl, isopropoxymethyl, butoxymethyl, isobutoxymethyl, tert-butoxymethyl, pentyloxymethyl, hexyloxymethyl, heptyloxymethyl, octyloxymethyl, decyloxymethyl, 2-methoxyethyl, 2-ethyloxyethyl, 2-propoxyethyl, 2-butoxyethyl, 2-hexyloxyethyl, 2-octyloxyethyl, 2-nonyloxyethyl, 3-methoxypropyl, 3-ethoxypropyl, 3-propoxypropyl, 3-butoxypropyl, 3-hexyloxypropyl, 3-octyloxypropyl, 3-decyloxypropyl, 4-methoxybutyl, 4-ethoxybutyl, 4-propoxybutyl, 4-butoxybutyl, 4-hexyloxybutyl, 4-octyloxybutyl, 4-nonyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 5-decyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 6-decyloxyhexyl, 8-methoxyoctyl, 8-ethoxyoctyl, 8-butoxyoctyl, 8-hexyloxyoctyl, 8-octyloxyoctyl, 10-methoxydecyl, 10-propoxydecyl, 10-pentyloxydecyl, and 10-decyloxydecyl.

Hydroxyalkyl means a hydroxy containing straight or branched chain alkyl group having 1 to 10 carbon atoms, and includes, for example, hydroxymethyl, 2-hydroxyethyl, 1-hydroxyethyl, 3-hydroxypropyl, 2-hydroxypropyl, 4-hydroxybutyl, 3-hydroxy-3-methylpropyl, 5-hydroxypentyl, 4-hydroxy-3-methylbutyl, 6-hydroxyhexyl, 8-hydroxyoctyl, and 10-hydroxydecyl.

Acyloxyalkyl means that acyloxy moiety and the alkyl moiety each are straight or branched chains having 1 to 10 carbon atoms, and includes, for example, acetoxym ethyl, acryloxymethyl, methacryloxymethyl, propionoxymethyl, acetoxyethyl, acryloxyethyl, butyroxyethyl, acetoxybutyl, acryloxybutyl, hexanoyloxybutyl, acetoxyhexyl, acryloxyhexyl, octanoyloxyhexyl, acetoxyoctyl, acryloxyoctyl, acetoxydecyl, and acryloxydecyl.

Substituted phenyl, tolyl, and benzyl means phenyl, tolyl, or benzyl ring substituted by at least one suitable substituent group selected from the group consisting of amino, nitro, hydroxy, straight or branched alkoxy group such as methoxy, straight or branched alkyl and/or fluoroalkyl group such as methyl, trifluoromethyl, alkenyl group such as vinyl, and halogen (fluorine, chlorine, bromine or iodine).

Representative examples of linear or branched alkyl and fluoroalkyl groups having 1 to 10 carbon atoms include, for example, methyl, trifluoromethyl, ethyl, 1,1,2-trifluoroethyl, pentafluoroethyl, propyl, perfluoropropyl, isopropyl, butyl, isobutyl, tert-butyl, perfluorobutyl, 1,1,2,3,3-pentafluorobutyl, pentyl, hexyl, heptyl, octyl, nonyl, and decanyl.

Linear or branched alkenyl means alkenyl moiety having 2 to 10 carbon atoms, and includes, for example, vinyl, 1-propenyl, allyl, isopropenyl, 2-butenyl, 1,3-butadienyl, 2-pentenyl, 2-hexenyl, 2-octenyl, 3-nonenyl, and 4-decenyl.

Substituted or unsubstituted, saturated or unsaturated fatty acid chain means a variety of long-chain fatty acids present in the oils as one of the triglycerides. These fatty acids may further be substituted by one or more substituents selected from the group consisting of alkyl, alkoxy, alkoxyalkyl, hydroxy, hydroxyalkyl, acyloxyalkyl, and halogens as described hereinabove. Illustrative examples of a few of these fatty acids include oleic acid, elaidic acid, linoleic acid, linolenic acid, erucic acid, brassidic acid, nervonic acid, lauric acid, myristic acid, palmitic acid, margaric acid, stearic acid, arachidic acid, behenic acid, lignoceric acid, cerotic acid, melissic acid and undecylenic acid.

Substituted acrylic means acrylic substituted by at least one substituent at the α- or β- position of the acrylic chain. Such a substituent is selected from the group consisting of methyl, ethyl, propyl, butyl, phenyl, and tolyl. Illustrative examples of substituted acrylic include methacrylic, ethacrylic, cinnamic, crotonic, isocrotonic, tiglic, and angelic.

A wide variety of linear or branched alkyl or alkenyl carboxylic acid moieties (as $R_{12}$ and $R_{13}$) having 2 to 30 carbon atoms are suitable for forming the internally plasticizing monomers of the present invention containing the multifunctional moiety II or III. Examples of such acids include acetic acid, propionic acid, n-butyric acid, n-hexanoic acid, n-heptanoic acid, octanoic acid, nonanoic acid, decanoic acid, lauric acid, myristic acid, palmitic acid, margaric acid, stearic acid, arachidic acid, behenic acid, lignoceric acid, cerotic acid, melissic acid and the like. Various other unsaturated fatty and non-fatty acids including the acrylic and substituted acrylics mentioned above may also be employed.

Monoalkyl esters of maleic and fumaric acids include, for example, methyl hydrogen maleate, methyl hydrogen fumarate, ethyl hydrogen maleate, ethyl hydrogen fumarate, propyl hydrogen maleate, propyl hydrogen fumarate, butyl hydrogen maleate, and butyl hydrogen fumarate.

Furthermore, and as used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As mentioned earlier, the preferred internally plasticizing monomers of this invention are derived (or obtained) from semi- or non-drying oils; that is, semi- or non-drying oils are subjected to suitable chemical or physical transformations to obtain these monomers. These starting materials may be obtained from natural sources such as vegetable or animal sources or may be synthetic. Thus, the starting materials which may be converted to the desired internally plasticizing monomers of this invention contain at least one hydroxy group in their backbone and have a terminal polar moiety (i.e., $R_8$ in I) selected from the group consisting of —CN, —COOR, —CH$_2$OH, —CH$_2$OR, —CONR'R", and —CH$_2$NR'R" where R, R', and R" have the same meaning as defined above. These terminal polar moieties may be introduced, if necessary, into the compounds obtained from semi- or non-drying oils using a number of well-known methods in the art. A description of a few of such methods may be found in U.S. Pat. No. 4,356,128 to Rogier, incorporated herein by reference in its entirety.

Briefly, the starting materials containing the terminal group, —COOR may be obtained by subjecting the oil to suitable transesterification reaction in the presence of an alcohol ROH. In this instance, the oil which is a triglyceride may also be used as such. Triglycerides are triesters of a glycerol formed by a combination of one or more fatty acids, and thus R in this case is a multifunctional moiety as defined above (i.e., II or III). The fatty compounds containing —CH$_2$OH or —CH$_2$OR terminal groups may be obtained by subjecting the corresponding fatty ester to suitable reductive conditions. If necessary, other groups vulnerable to such reductive conditions may suitably be protected before subjecting the fatty ester to reductive conditions.

Similarly, compounds having —CONR'R" (i.e., amides) may be obtained by the reaction of corresponding carboxylic acids (or the carboxylic acid halides such as carboxylic acid chloride) obtained from the oils with an amine, HNR'R" under suitable reaction conditions. Further subjecting so formed amides to suitable reduction reactions results in the formation of compounds having —CH$_2$NR'R" group.

The compounds with the —CN group, for example, may be obtained by first reacting the fatty acid chlorides with ammonia to form the corresponding amides having the terminal group, —CONH$_2$. The amides so formed can subsequently be dehydrated using a number of well-known dehydrating agents known in the art to form the corresponding —CN containing compounds.

The preferred hydroxy fatty acids that are suitable for forming the long-chain olefinic ester I may be selected from the group consisting of ricinoleic, lesquerolic, auricolic, and densipolic acid. All of these acids contain one hydroxy group and at least one double bond in their back bone. If the starting material employed in the latex or emulsion compositions of the present invention is a triglyceride, then various other fatty acids may be employed as $R_{12}$ and $R_{13}$ in the triglyceride (i.e., II or III). The preferred fatty acids that may be employed for forming the desired triglycerides may be selected from the group consisting of oleic, linoleic, erucic, and vernolic acid.

However, the fatty acids obtained from the drying oils as such are not suitable for forming the triglycerides that are suitable as starting materials of this invention (i.e., I). In general, fatty acids containing more than two double bonds in their back bone are not suitable starting materials for this invention without further derivation as described hereinbelow. Such fatty acids, for example, include linolenic, eleostearic, licanic, and isanic acid. Accordingly, the non-drying oils are generally more preferred in this invention and include, for example, cottonseed, coconut, rapeseed, lesquerella, castor, and vernonia oil. The non-drying oils which contain no hydroxy groups in their backbone may be suitably functionalized so as to result in at least one hydroxy group in their backbone. For example, U.S. Pat. No. 4,626,582 describes synthesis of hydroxymethyl containing fatty compounds; and U.S. Pat. No. 5,312,889 describes formation of a hydroxy group using an unsaturated fatty compound by epoxidation and reductive ring opening, which are incorporated herein by reference in their entirety. Similarly, drying oils can be suitably transformed into hydroxy fatty acids or their derivatives having an iodine value of 150 or less such that they can be used as semi- and/or non-drying oil components of this invention. Particularly preferred non-drying oils are castor and lesquerella oils.

A wide variety of ethylenically unsaturated carboxylic acids or its derivatives may be used for the formation of desired starting materials of the present invention. The carboxylic acids having at least one polymerizable ethylenic bond per molecule (i.e., a double bond) are preferred. The acids with an ethylenic bond α,β- (i.e., 1,2-) to the carboxylic group are particularly preferred. Representative examples of such ethylenically unsaturated carboxylic acids include, without limitation, acrylic, methacrylic, maleic, fumaric, itaconic, ethacrylic, crotonic, citraconic, cinnamic, methyl hydrogen fumarate, benzyl hydrogen maleate, butyl hydrogen maleate, octyl hydrogen itaconate, and dodecyl hydrogen citraconate. If the acid employed is a dicarboxylic acid, such as maleic acid or fumaric acid, then the resulting starting material is a diester of a desired long-chain olefinic monomer.

The compositions containing the long-chain olefinic monomers of the present invention further consists of at least one copolymerizable monomer. Such a copolymerizable monomer include, broadly, polymerizable acid monomer, a monomer containing at least one ethylenically unsaturated polymerizable group, and various other ethylenically unsaturated monomers well known in the art.

Polymerizable acid monomers used in this invention are the well known mono- or polycarboxylic acids which contain one polymerizable bond per molecule. Examples of such acids are acrylic acid, methacrylic acid, maleic acid, fumaric acid, itaconic acid, ethacrylic acid, crotonic acid, citraconic acid, and half esters of the dicarboxylic acids wherein the esterified alcohol group contains from 1 to about 20 carbon atoms. Examples of suitable half esters are methyl hydrogen maleate, methyl hydrogen fumarate, benzyl hydrogen maleate, butyl hydrogen maleate, octyl hydrogen itaconate, dodecyl hydrogen citraconate, and the like. Carboxylic acid anhydrides such as maleic anhydride can also be used. The preferred acids for use in this invention are acrylic and methacrylic acids.

Copolymerizable monomers that contain at least one ethylenically unsaturated polymerizable group referred to hereinabove are any of the well known monomers which contain at least one ethylenically unsaturated polymerizable group per molecule and are copolymerizable with the other monomers. Examples of such monomers are acrylic and methacrylic esters wherein the ester group contains 1 to about 20 carbon atoms, e.g., methyl acrylate, methyl methacrylate, ethyl acrylate, ethyl methacrylate, isopropyl acrylate, isopropyl methacrylate, butyl acrylate, butyl methacrylate, 2-ethylhexyl methacrylate, decyl acrylate, lauryl methacrylate, benzyl acrylate, and the like. Esters of various other unsaturated acids include butyl fumarate, octyl fumarate, butyl maleate, and octyl maleate.

Other acrylic or methacrylic esters which can be used in this invention are multifunctional acrylates or methacrylates, and includes, for example, propylene glycol monoester of acrylic acid, propylene glycol monoester of methacrylic acid, ethylene glycol monoester of acrylic acid, ethylene glycol monoester of methacrylic acid, glycidyl acrylate, glycidyl methacrylate, hydroxyethyl acrylate, hydroxyethyl methacrylate, and hexanediol diacrylate.

Other copolymerizable monomers are vinyl aromatic monomers, such as styrene, para-acetoxystyrene, vinyl toluene, alpha methyl styrene, vinyl pyridine and the like as well as nitriles and amides, e.g., acrylonitrile and acrylamide. Other olefinic monomers such as ethylene, propylene, and butadiene are also suitable comonomers for this invention.

Additional copolymerizable monomers that can be used in this invention are the derivatives of the hypothetical vinyl alcohol, i.e., aliphatic vinyl esters such as vinyl formate, vinyl acetate, vinyl propionate, vinyl butyrate, vinyl heptanoate, vinyl pelargonate, vinyl 3,6-dioxaheptanoate, vinyl 3,6,9-trioxaundecanoate, the vinyl ester of versatic acid (sold under the tradename Veova 10™), vinyl esters of neo acids and the like. Other vinyl monomers such as vinyl chloride, vinyl sulfonate, vinyl silanes, and vinylidene chloride are also suitable comonomers.

Various other copolymerizable monomers that impart enhanced properties to the resulting compositions of the present invention may also be used. One such example is a wet adhesion promoter which improves adhesion of the compositions to a wide variety of substances including wood, plastic, and metal surfaces. Illustrative examples of such wet adhesion promoting monomers include dimethylaminoethyl methacrylate, methacrylamidoethylethyleneurea (sold under the tradename Sipomer® WAM II by Rhone-Poulenc), acrylamidoethylethyleneurea, 3-isopropenyl-α,α-dimethylbenzyl isocyanate, and styrene sulfonate.

Any monomers which are copolymerizable with the ethylenically unsaturated long-chain olefinic monomer I of this invention can be used in this invention. Such monomers are those which contain no groups which are reactive under polymerization conditions with carboxylic acid groups, —COOR, —CH$_2$OH, —CH$_2$OR, —CN, —CONR'R", or —CH$_2$NR'R" groups. Thus, suitable comonomers may be employed depending upon the groups present in the long-chain olefinic monomer I.

The types and amounts of copolymerizable monomers used in this invention will vary depending on the particular end use for which the product of this invention is intended. Such variations are well known and can be readily determined by those skilled in the art. In general, the weight percents of the internally plasticizing compound, i.e., the long-chain olefinic monomer I and the copolymerizable monomer in the resulting composition ranges from about 5 and not more than about 80 weight percent based upon the total weight of the composition. Preferably, the total weight percents range from about 30 to about 70 weight percent based on the total weight of the composition. The weight ratio of the long-chain olefinic monomer I to the copolymerizable monomer (s) generally range from about 1:2 to about 1:99, preferably the weight ratio range from about 1:7 to about 1:20.

In addition to the polymeric resins formed from the monomer I and the comonomers mentioned hereinabove, the coatings or adhesives or inks compositions of the present invention contain at least one drier. The driers are materials that promote or accelerate the curing or hardening of film formers. Typically, driers are used in conjunction with coatings formulations containing the drying oil components. Surprisingly, it has now been found that the metal driers are particularly effective in curing the compositions of the present invention which contain semi- or non-drying oil components.

The suitable drier is any material which will function as a promoter or an accelerator for the curing or hardening of the film and includes, without limitation, neutral soaps of the formula $(R_x$—COO$)_2$M$^{2+}$ or $(R_x$—COO$^-)_3$M$^{3+}$; acid soaps of the formula $(R_x$—COO$^-)_2$M$^{2+}$. $R_x$—COOH or $(R_x$—COO$^-)_3$M$^{3+}$. $R_x$—COOH; basic soaps of the formula $(R_x$—COO$^-)_2$M$^{2+}$. OH; organic complexed or mixed soaps of the formula $(R_x$—COO$^-)(R'_x$—COO$^-)$M$^{2+}$ or $(R_x$—COO$^-)(R'_x$—COO$^-)(R''_x$—COO$^-)$M$^{3+}$; inorganic/organic complexed or mixed soaps of the formula O—M$^{2+}$—O—CO—R$_x$, X—O—M$^{2+}$—O—CO—R$_x$, and O—M$^{2+}$—O—CO—R$_x$; where $R_x$—COO$^-$, $R'_x$—COO$^-$; and $R''_x$—COO$^-$ are aliphatic carboxylic acid ions having 6 to 20 carbon atoms, M=metal ion, and X=phosphorus or boron.

The commonly used carboxylic acids for forming the metal driers are aliphatic acids, preferably fatty acids. Illustrative examples of fatty acids include rosin oil fatty acid, linseed oil fatty acid, and tall oil fatty acid. Various naphthenic acids obtained from certain petroleum crudes may also be used for forming the suitable metal driers. The naphthenic acids generally contains an average of 12–14 carbon atoms having a cyclopentane nucleus with the carboxyl group terminating a side chain and with one to three methylenic groups between the carboxyl and the nucleus. Various other synthetic acids having 8 to 10 carbon atoms are also used to form the metal driers, and include, for example, 2-ethylhexanoic acid and neodecanoic acids.

The most commonly used drier metals are cobalt, zirconium, manganese, calcium and lead. Other metals such as zinc, copper, barium, vanadium, cerium, iron, potassium, strontium, aluminum, bismuth, and lithium have also been used as drier metals. Particularly preferred metal driers are aliphatic carboxylic salts of cobalt, manganese, lead, zirconium, calcium, and mixtures thereof It has been found that cobalt salts sold under the tradename Co Hydro-Cure® II are particularly preferred metal driers for the compositions of the present invention. A detailed description of various metal driers may be found in "Surface Coatings—Raw Materials and Their Usage," Vol. I, Chapman & Hall, Chapter 33, pp 592–606 (1993), incorporated herein by reference in its entirety.

Although metal driers mentioned hereinabove are particularly effective in the drying of the films, various other non-metallic driers well-known in the art may also be employed either as primary driers, auxiliary driers, or as drier accelerators. Many auxiliary non-metallic driers are effective in improving the solubility of the active drier metal in the reactive medium or alter the drier metals' redox potential. Examples of such non-metallic driers include 8-hydroxyquinoline, quinoline, salicyl aldoxime, pyridine-2-carbaldoxime, acetylacetonate enamines, 2-2'-bipyridyl, ethylenediamine, propylenediamine, pyridine, o-vinylpyridine, o-aminopyridine, aniline, o-phenylenediamine, o-toluidine, α-naphthylamine, o-phenanthroline, dipropylamine, diamylamine, acrylonitrile, succinonitrile, o-tolunitrile, o-toluamide, o-tolyl isocyanate, phenyl isocyanate, naphthyl isocyanate, pyrrole, benzimidazole, benzotriazole, and the like. Particularly preferred non-metallic drier is 2-2'-bipyridyl sold under the tradename DRI-RX™.

As described hereinbelow, the compositions of this invention are prepared by polymerization of monomers emulsified in water using conventional emulsion polymerization procedures. A suitable surface-active agent generally known as surfactants are used for emulsification of the monomers. Suitable surfactants include cationic, anionic, amphoteric, or nonionic surfactants or mixtures thereof.

Examples of useful anionic surfactants are organosulfates and sulfonates, e.g., sodium and potassium alkyl, aryl, and aralkyl sulfates and sulfonates, such as sodium 2-ethylhexyl sulfate, potassium 2-ethylhexyl sulfate, sodium nonyl sulfate, sodium lauryl sulfate, potassium methylbenzene sulfonate, sodium dodecylbenzene sulfonate, potassium toluene sulfonate and sodium xylene sulfonate; higher fatty alcohols, e.g., stearyl, lauryl, etc., which have been ethoxylated and sulfonated; dialkyl esters of alkali metal sulfosuccinic acid salts, such as sodium diamyl sulfosuccinate, sodium dioxtyl sulfosuccinate, and sodium dioctyl sulfosuccinate, formaldehyde-naphthalene sulfonic acid condensation products; and alkali metal salts, partial alkali metal salts and free acids of complex organic phosphate esters.

Examples of useful cationic surfactants include alkylamine salts such as laurylamine acetate, quaternary ammonium salts such as lauryl trimethyl ammonium chloride and alkyl benzyl dimethylammonium chlorides, and polyoxyethylenealkylamines. Examples of the amphoteric surfactants are alkylbetaines such as lauryl-betaine.

Examples of nonionic surfactants which can be used in this invention are polyethers, e.g., ethylene oxide and propylene oxide condensates which include straight and branched chain alkyl and alkaryl polyethylene glycol and polypropylene glycol ethers and thioethers; alkylphenoxypoly(ethyleneoxy) ethanols having alkyl groups containing from about 7 to about 18 carbon atoms and having from about 4 to about 240 ethyleneoxy units, such as heptylphenoxypoly(ethyleneoxy) ethanols, nonylphenoxypoly(ethyleneoxy) ethanols; the polyoxyalkylene derivatives of hexitol including sorbitans, sorbides, mannitans and mannides; partial long-chain fatty acids esters, such as the polyoxyalkylene derivatives of sorbitan monolaurate, sorbitan monopalmitate, sorbitan monostearate, sorbitan tristearate, sorbitan monooleate and sorbitan trioleate; the condensates of ethylene oxide with a hydrophobic base, said base being formed by condensing propylene oxide with propylene glycol; sulfur containing condensates, e.g., those prepared by condensing ethylene oxide with higher alkyl mercaptans, such as nonyl, dodecyl, or tetradecyl mercaptan, or with alkylthiophenols wherein the alkyl group contains from about 6 to about 15 carbon atoms; ethylene oxide derivatives of long-chain carboxylic acids, such as lauric, myristic, palmitic, or oleic acids or mixtures of acids, such as tall oil fatty acids; ethylene oxide derivatives of long-chain alcohols such as octyl, decyl, lauryl, or cetyl alcohols; and ethylene oxide/propylene oxide copolymers sold under the tradename Pluoronics™.

A particularly useful surfactant which can be used in this invention is a nonionic surfactant which is an organosilanol derivative of tung oil, or linseed oil, or high erucic acid rapeseed oil. These surfactant compositions particularly feature high surface activity in forming stable emulsions of organic/water of various difficultly emulsifiable materials as compared with conventional emulsifying agents. These silanol-based surfactant compositions are described in copending, commonly assigned patent application Ser. No. 08/739,850, filed Oct. 30, 1996. Another class of preferred surfactants are those which are copolymerizable with the monomers described hereinabove.

The amounts of surfactants employed in the emulsion polymerization process will range from about 0.01 to about 10 weight percent, preferably about 0.2 to about 5 weight percent based on the total weight of monomers and water.

The compositions of the present invention may contain in addition to the polymeric resins and metal driers referred to hereinabove, as required, suitable additives such as protective colloids, fillers, coloring agents, antiseptics, biocides, dispersing agents, thickening agents, thixotropic agents, antifreezing agents, and pH adjusting agents.

Examples of protective colloids are partially and fully hydrolyzed polyvinyl alcohol, hydroxyethyl cellulose, hydroxymethyl cellulose, ethylhydroxyethyl cellulose, carboxymethyl cellulose, ethoxylated starch derivatives, polyacrylic acid, alkali metal polyacrylates, polyacrylamide, poly(methyl vinyl ether/maleic anhydride), polyvinylpyrrolidone, water soluble starch, glue, gelatin, water soluble alginates, guar, gum arabic and gum tragacanth. The amounts of protective colloids used in the composition varies depending upon the intended application and generally ranges from about 0.1 weight percent to about 2 weight percent based on the total weight of the composition.

Examples of fillers include talc, calcium carbonate, diatomaceous earth, mica, kaolin, barium sulfate, magnesium carbonate, Aerosil, vermiculite, graphite, alumina, silica and rubber powder. Such coloring agents as titanium dioxide and carbon black can also be used as the fillers. The amount of the filler may be properly selected, and when used, for example, ranges from about 10 weight percent to about 50 weight percent based on the total weight of the composition of the present invention.

Various organic pigments and inorganic pigments may be broadly used as the coloring agents, but non-toxic anticorrosive pigments are preferred. Examples of such pigments are phosphate-type anticorrosive pigments such as zinc phosphate, calcium phosphate, aluminum phosphate, titanium phosphate, silicon phosphate, and ortho- and fused phosphates of these; molybdate-type anticorrosive pigments such as zinc molybdate, calcium molybdate, calcium zinc molybdate, potassium zinc molybdate, potassium zinc phosphomolybdate and potassium calcium phosphomolybdate; and borate-type anticorrosive pigments such as calcium borate, zinc borate, barium borate, barium meta-borate and calcium meta-borate. The amount of the coloring agent used may also be properly selected based on the end-use application of the compositions of the present invention.

Examples of the antiseptics are pyrrole compounds, imidazole compounds, thiazole compounds, pyridine compounds and organic halogen compounds. The amount of the antiseptic can be suitably selected, and is, for example, up to about 4 percent by weight based on the total weight (as solids content) of the composition.

Examples of the biocides, which are used either as wet-state protectors (i.e., in-can protectors) or as film protectors of a coating composition, are a wide variety of bactericides, fungicides or algicides, and include, without limitation, zinc oxide, cuprous oxide, organotin pigments, copolymers of organotin esters of methacrylic acid with conventional acrylates, tributyl tin oxide, and mixtures thereof Other examples of biocides particularly useful as in-can protectors are oxazoladines, organosulfurs, and benzisothiazolins. Any general toxic agent may be suitable as a biocide.

The dispersing agents may, for example, be inorganic dispersing agents such as sodium salts of polycarboxylic acids, sodium or ammonium salt of fused naphthalene sulfonate, polyoxyalkylene alkyl ethers of phenol ether, sorbitan fatty acid esters, polyoxyalkylene fatty acid esters, glycerin fatty acid esters, polyoxyethylene styrene phenol, sodium tripolyphosphate and sodium hexametaphosphate. As mentioned above, novel organosilanol derivatives of tung oil, or linseed oil, or high erucic acid rapeseed oil which are useful as surfactants are also suitable as dispersing agents. The amount of the dispersing agent can again be properly selected depending on the end application of the composition, and may range up to about 10 weight percent based on the total weight of the composition.

The thickening and thixotropic agents may be one and the same or different and may be the same as the protective colloids referred to hereinabove. Examples of thickening or thixotropic agents are polyvinyl alcohol, cellulose derivatives such as hydroxyethyl cellulose, hydroxypropyl cellulose and carboxymethyl cellulose salt, polyether compounds, urethane-modified polyether compounds, polycarboxylic acid compounds, sodium salts of polycarboxylic compounds, polyvinylpyrrolidone, polyoxyethylene derivatives such as polyethylene glycol ether and polyethylene glycol distearate, sodium alginate and inorganic materials such as sodium silicate and bentonite. The amounts of the thickening or the thixotropic agents can be properly chosen depending upon the type of end-application of the composition of the present invention.

Examples of the pH adjusting agents are sodium hydroxide, potassium hydroxide, sodium hydrogen carbonate, ammonia, triethanolamine, and β-dimethylaminoethanol. The amount of the pH adjusting agent may be a suitable one which is sufficient to adjust the pH of the composition to a desired value.

Various other additives having functional applications in coatings which are well known to those skilled in the art may also be used with the compositions of the present invention. Specific examples of such functional additives are corrosion inhibitors, ultraviolet light stabilizers, antioxidants, and the like.

Thus, in one of the specific embodiments of this invention the total solids content including the internally plasticizing compound, i.e., the long-chain olefinic monomer I, copolymerizable monomers, and all of the desirable additives referred to hereinabove is preferably ranging from about 30 to about 70 percent by weight based on the total weight of the composition.

In another specific embodiment of this invention, the composition suitable for forming latex or emulsion coatings comprises an internally plasticizing compound derived (or obtained) from a non-drying oil having a substituted ethylenically unsaturated carboxylic acid ester of a long-chain olefinic ester of the formula IV.

present invention, the compositions exhibit lower METs and cure to resins having $T_g$s significantly higher than the MFTs. A further significance of this invention is the capability of tailoring the glass transition temperature ($T_g$) of the emulsion polymers and the MFTs of the compositions formed therefrom. The METs of a coating composition is determined experimentally by using an apparatus described by Protzman et al. in *J. Appl. Polymer Sci.*, 4, 81 (1960) incorporated herein by reference in its entirety. This apparatus is essentially an aluminum slab in which a constant and uniform temperature gradient may be maintained. The coating composition to be measured is spread uniformly in one of several sample wells. The point at which the film becomes discontinuous when dry is observed and this temperature is recorded as the MFT. To ensure that the films are actually continuous when formed above the MFT, the films are scrapped with a knife edge moving in the direction from low to high temperature. Below the MFT the material chips off the bar easily but above the MET the coating does not lift off

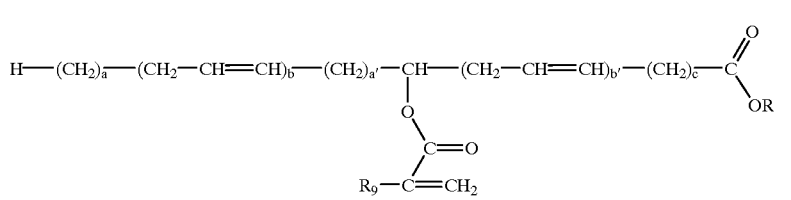

IV

Where R and $R_9$ are as defined above, however, preferably R is either methyl or multifunctional moieties II or III. Preferred $R_9$ is either hydrogen or methyl, i.e., ethylenically unsaturated ester in this preferred embodiment is either acrylic or methacrylic ester. a, a', b, b', and c, in structure IV are integers, where a and a' have a value of from 2 to 4, b and b' have a value of 0 to 2 with the proviso that sum of b and b' is 1 or 2, and c has a value of 5 to 12.

The preferred copolymerizable monomers in this embodiment may be selected from the group consisting of vinyl acetate, vinyl chloride, vinyl ester of versatic acid, acrylonitrile, acrylamide, 2-ethylhexyl acrylate, 2-ethylhexyl methacrylate, 2-hydroxyethyl acrylate, 2-hydroxyethyl methacrylate, glycidyl acrylate, glycidyl methacrylate, acrylic acid, butyl acrylate, butyl methacrylate, methyl methacrylate, methyl acrylate, and styrene. Various combinations of one or more of anionic, cationic, amphoteric, or nonionic surfactants may be used in this embodiment.

The starting materials for the preferred long-chain olefinic ester IV in the above embodiment is derived (or obtained) from either castor oil or lesquerella oil, or the transesterified product obtained from either castor oil or lesquerella oil with methanol. Thus, the long-chain olefinic ester IV may be formed from appropriate starting material by subjecting it to suitable esterification reaction as described below.

Thus, the preferred starting material for the formation of IV may be selected from the group consisting of castor oil, lesquerella oil, transesterified product of castor oil with methanol, transesterified product of lesquerella oil with methanol, methyl ricinoleate, and methyl lesquerolate. Accordingly, the products formed from these starting materials which are the preferred long-chain olefinic esters IV are acrylate ester of methyl ricinoleate, methacrylate ester of methyl ricinoleate, acrylate ester of methyl lesquerolate, and methacrylate ester of methyl lesquerolate.

As stated earlier, by incorporation of the internally plasticizing monomers (i.e., I or IV) into compositions of the the bar. The transition between easily chipped to strong coating takes place at the MFT.

Conventional latex polymers generally feature MFTs closer to their $T_g$. Contrary to this conventional norm, the compositions of the present invention exhibit MFTs much below the final $T_g$ of the cured and crosslinked emulsion polymer contained therein, thus eliminating the need for a plasticizer which is generally a volatile organic compound (VOC). Particularly, the compositions of the above mentioned preferred embodiment forms film at low MFTs ranging from about −5 to about 10° C. and cures to a resin having a $T_g$ higher than 25° C.

The compositions of the present invention are particularly useful as coatings, adhesives, and inks formulations. A wide variety of coating formulations may be formed from the compositions of this invention. In general, the coating compositions are formed by incorporating the emulsion polymers formed from the internally plasticizing compound with one or more of the copolymerizable monomers described hereinabove. In addition, the coating compositions contain at least one drier and a surfactant, and as required, one or more of the additives described hereinabove.

The coatings produced by the cure of the internally plasticizing compound of this invention are useful in a wide variety of applications, i.e., architectural, decorative, maintenance, or industrial coatings. For example, in the electronics area these materials have applications as non-conductive coatings, e.g., solder masks for circuit boards or moisture resistant coatings for the boards or optical fibers.

Similarly, the compositions of the present invention may be formulated into a wide variety of adhesives and inks formulations having a diverse variety of applications. For example, in inks formulations the emulsion polymers of this invention are useful as binders. In general ink formulation differs from coating formulations in terms of the amounts of crosslinking monomers used, i.e., ink formulations generally contain higher amounts of the crosslinker. In addition, ink formulations may contain higher amounts of driers and drier accelerators for fast drying of these formulations. Accordingly, an ink formulation containing the emulsion polymers of this invention may be obtained by adding one or more pigments to the emulsion in accordance with a well-known method. The compositions of this invention may also be employed in forming radiation curable formulations, for example, UV curable high gloss coatings, inks, and adhesives formulations.

An adhesive formulation containing the emulsion polymers of this invention may similarly be obtained in accordance with a well-known method. Typically, an adhesive formulation may be formed using the emulsion polymer of this invention in combination with one or more of surfactants, protective colloids, and one or more of various other additives discussed hereinabove. The adhesive formulations of this invention are particularly suitable in the form of emulsion and/or aqueous solution, however, dry-mix, hot-melt, or solutions in organic solvent can also be formed using the polymers of this invention. A detailed description of adhesive formulations can be found in "*Handbook of Adhesives,*" 2nd Ed., edited by I. Skiest, Chapter 28, pp 465–494 (1977), Van Nostrand Reinhold Co., incorporated herein by reference in its entirety.

In a further aspect the invention provides a process for the formation of a waterborne formulation for coatings, inks or adhesives containing a latex formed from an ethylenically unsaturated ester of a long-chain olefinic monomer derived from a semi- or non-drying oil comprising the steps of:

(a) subjecting a substituted long-chain olefinic compound having a hydroxy group to suitable esterification conditions in the presence of an ethylenically unsaturated carboxylic acid or its suitable derivative for a sufficient period of time and under suitable conditions of temperature and pressure to form the corresponding ethylenically unsaturated ester of a long-chain olefinic monomer;

(b) subjecting said ester of a long-chain olefinic monomer to suitable polymerization conditions in the presence of at least one other ethylenically unsaturated copolymerizable monomer for a sufficient period of time and under suitable conditions of temperature and pressure to form the corresponding polymer dispersed in an aqueous phase; and (c) blending said dispersion of said polymer with at least one drier selected from the group consisting of aliphatic carboxylic acid salts of cobalt, manganese, lead, zirconium, calcium, and mixtures thereof, and in the presence of at least one ionic or non-ionic surface-active agent to form the formulation.

The starting material, i.e., the long-chain olefinic compound V is the same compound as described hereinabove and is derived (or obtained) from a semi- or non-drying oil.

(V)

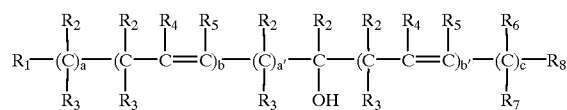

Where $R_1$, $R_2$, $R_3$, $R_4$, $R_5$, $R_6$, $R_7$, $R_8$, a, a', b, b', and c are as defined above. The preferred starting materials are those having $R_8$=—COOR and most preferably derived (or obtained) from the group consisting of ricinoleic, lesquerolic, auricolic, and densipolic acids. These fatty acids are preferably obtained from non-drying oils such as castor oil or lesquerella oil.

The esterification reaction of V and an ethylenically unsaturated carboxylic acid or its derivative VI may be carried out using any of the well-known methods in the art. In the structure VI, $R_9$, $R_{10}$, and $R_{11}$ are as defined above. X is selected from the group consisting of Br, Cl, hydroxy, alkoxy group having 1 to 4 carbon atoms, and acyloxy group same as the acyloxy group derived from said ethylenically unsaturated carboxylic acid or an acyloxy group having 2 to 4 carbon atoms as described hereinabove.

(VI)

Accordingly, the esterification reaction in the step (a) of the process of the present invention may be generically represented as follows:

(Eq. 1)

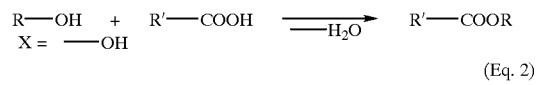

(Eq. 2)

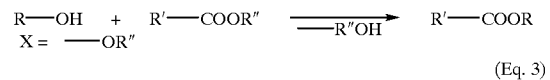

(Eq. 3)

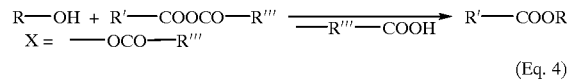

(Eq. 4)

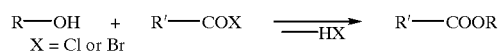

In this schematic representation, R'—CO is an acyl group of the ethylenically unsaturated carboxylic acid or its derivatives of formula VI, R–O— refers to the alkoxy group and R'"—COO refers to the acyloxy group mentioned hereinabove. In most instances the esterification reaction is carried out by using one mole of the acid or its derivative VI per mole of hydroxy group present in V. However, it may be desirable to use one of these starting materials in excess of the other in some cases.

The preferred ethylenically unsaturated carboxylic acid and its derivatives VI are either acrylic or methacrylic derivatives, i.e., $R_{10}$ and $R_{11}$ are hydrogen and $R_9$ is either methyl or hydrogen in VI. Accordingly, the preferred acryloyl or methacryloyl compound used to esterify the hydroxy long-chain compound V is a halide such as acryloyl chloride, methacryloyl chloride, acryloyl bromide, and methacryloyl bromide. Various other acryloyl or methacryloyl derivatives that may be employed in this esterification reaction include acrylic acid, methacrylic acid, methyl acrylate, methyl methacrylate, ethyl acrylate, ethyl methacrylate, n-propyl acrylate, butyl acrylate, acrylic anhydride, methacrylic anhydride, mixed anhydrides of acrylic and acetic acids, and the like.

The esterification reaction may be carried out with or without any catalysts. However, in some cases it is preferable to carry out the esterification reaction in the presence of a suitable acid, base or metal catalysts. Any acid, base or metal catalyst that will function as a catalyst for the esterification conditions may be used in this step (a) of the process of the present invention. Specific examples of such esterification reactions may be found in U.S. Pat. Nos. 4,745,213 and 5,243,069, incorporated herein by reference in their entirety.

The suitable acid includes, without limitation, mineral acids such as HCl and $H_2SO_4$; super acids such as hydrofluoric acid, fluorosulfonic acid; organic sulfonic acids such as p-toluene sulfonic acid, methane sulfonic acid, and trifluoromethane sulfonic acid; other inorganic acids such as phosphoric acid, and boric acid; carboxylic acids such as trifluoro acetic acid; Lewis acids such as $BF_3$, $AlCl_3$, $SbF_5$, and the like; and solid acid catalysts such as silica, zeolites, and the like. The suitable base includes an inorganic base such as a metal hydroxide, preferably an alkali metal hydroxide, an alkali metal carbonate, e.g., $K_2CO_3$; an alkali metal alkoxide (an ionic organic base), such as $NaOCH_3$, $KOC(CH_3)_3$, etc.; an alkali metal organic salt (an ionic organic base) such as potassium acetate, etc.; and an amine (a non-ionic organic base) such as pyridine, or a tri-loweralkylamine, e.g., tripropylamine, trimethylamine, triethylamine, an hindered base such as 2,4-diazabicyclo[2, 2,2]octane, etc. Ammonia can also be used as a base in step (a) of the process of the present invention.

Illustrative examples of metal catalysts that are particularly suitable in the transesterification type reactions (i.e., Eq. 2) include derivatives of Group I metals, derivatives of Group IVA metals, derivatives of Group IVB metals, derivatives of manganese and cobalt, and mixtures thereof These may be preferably lithium acetate, sodium acetate, potassium acetate, cesium acetate, stannic acid, butylstannoic acid, stannous octanoate, dibutyltin oxide, tin butoxide, dibutyltin diesters, di-n-butyl tin dilaurate, titanium tetrabutoxide, titanium propoxide, titanium phenoxide, zirconium butoxide, silicon phenoxide, manganese acetate, cobalt acetate, and mixtures thereof.

The amount of the catalyst employed depends upon the nature of the esterification reaction and the catalyst. Any amount of catalyst that would be sufficient to carry out the desired esterification reaction may be used and may range from about 30 parts per million to one to two moles of catalyst per mole of the acid or its derivative VI used in this reaction.

The temperature at which step (a) is conducted ranges from about $-10°$ C. to about $150°$ C., preferably from about $10°$ C. to about $100°$ C. The pressure in this step (a) is not critical and can be subatmospheric, atmospheric, or super atmospheric.

The reaction times in step (a) will generally range from about 15 minutes to about 6 hours or longer and sometimes under an inert atmosphere such as nitrogen.

Using the procedure of step (a) outlined herein, the hydroxy long-chain olefinic compound V undergoes esterification reaction with carboxylic acid or its derivatives VI to form the corresponding ethylenically unsaturated ester of a long-chain olefinic monomer I.

In step (b) of the process of the present invention the olefinic monomer I is subjected to suitable emulsion polymerization conditions in the presence of one or more of suitable copolymerizable monomers having at least one polymerizable ethylenically unsaturated double bond. The suitable copolymerizable monomers of this invention are those which are described hereinabove. The polymerization of these monomers emulsified in water can be carried out using conventional emulsion polymerization procedures. Typically such polymerization reactions are carried out in the presence of one or more anionic, cationic, amphoteric, or nonionic surfactants. The suitable surfactants are those which are described hereinabove.

The monomers, i.e., the monomer I and the copolymerizable monomers of this invention are polymerized by means of a catalytic amount of a conventional free radical polymerization catalyst or catalyst system (which can also be referred to as an addition polymerization catalyst, a vinyl polymerization catalyst, or a polymerization initiator), preferably, one which is substantially water soluble. Among such catalysts are peroxides, such as hydrogen peroxide, tertiary butyl hydroperoxide, cumene hydroperoxide; alkali metal (e.g., sodium, potassium, or lithium), and ammonia persulfates, perphosphates, and perborates; azo nitriles, such as $\alpha,\alpha$-azobisisobutyronitrile, and water soluble azo initiators, such as WAKO™ initiators; and redox system including such combinations as mixtures of hydrogen peroxide, t-butyl hydroperoxide or the like, and any of the iron salts, titanous salts, zinc formaldehyde sulfoxylate, or sodium formaldehyde sulfoxylate; alkali metal or ammonium persulfate, perborate, or perchlorate together with an alkali metal bisulfite, such as sodium metabisulfite; and alkali metal persulfate together with an aryl phosphinic acid such as benzene phosphinic acid and the like.

The temperature at which step (b) is conducted ranges from about $10°$ C. to about $90°$ C., preferably from about $20°$ C. to about $75°$ C. The pressure in this step (b) is not critical and can be subatmospheric, atmospheric, or super atmospheric.

The reaction times in step (b) will generally range from about 1 hour to about 6 hours or longer and sometimes under an inert atmosphere such as nitrogen.

Using the procedure of step (b) outlined herein, the ethylenically unsaturated ester of a long-chain olefinic monomer I undergoes polymerization reaction with one or more of copolymerizable monomers to form the polymers dispersed in water.

In step (c) of the process of this invention the polymer so formed in step (b) still dispersed in water is further blended with at least one or more of a metal drier, surfactant, and desired combinations of the additives to form the waterborne formulations suitable for use in coatings, adhesives or inks applications. For instance, the suitable metal driers, surfactants, and various additives are those described hereinabove. The amounts of these components used depend on the intended use of the formulation and generally range in amounts as described hereinabove.

The blending in step (c) can be carried out in any of the mixing/blending devices generally known in the art. The temperature at which the blending is conducted is generally around ambient conditions, and ranges from about $10°$ C. to about $40°$ C. The reaction times for blending generally range from about 10 minutes to about 60 minutes and sometimes under an inert atmosphere such as nitrogen.

Thus, in one of the preferred embodiments of this invention a process for the preparation of a coating composition using the internally plasticizing compound IV is also provided. Using the process of this invention described hereinabove the coating composition is prepared in this embodiment utilizing the compound IV. Accordingly, the compound IV is first prepared employing a corresponding hydroxy fatty acid ester and a substituted or unsubstituted acrylic acid or its derivatives using appropriate esterification conditions discussed hereinabove. The compound IV is then polymerized with one or more of copolymerizable monomers using an emulsion polymerization conditions, and in the final step blended with one or more of driers and other desirable additives to form the coating composition.

In yet another aspect the invention provides novel compounds suitable as internally plasticizing monomers of this invention for forming the novel latex or emulsion compositions described hereinabove. These monomers are substituted ethylenically unsaturated carboxylic acid esters of long-chain olefinic compounds of the formula Ia:

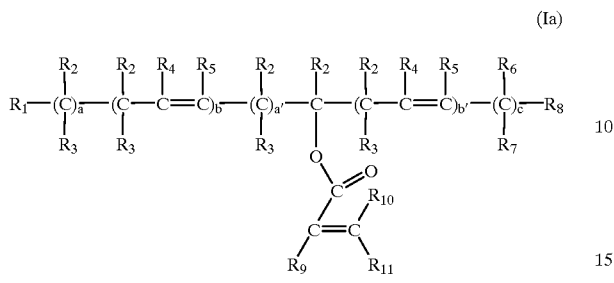
(Ia)

Where $R_1$, $R_2$, $R_3$, $R_4$, $R_5$, $R_7$, $R_9$, $R_{10}$, $R_{11}$, a, b, and c are as defined above. $R_8$ is selected from the group consisting of —CN, —CONR'R", and —CH$_2$NR'R", —CH$_2$OH, —CH$_2$OR, where R, R', and R" are as defined above. The preferred monomers are unsubstituted wherein $R_1$, $R_2$, $R_3$, $R_4$, $R_5$, $R_6$, $R_7$ are hydrogen and are derived from fatty acids obtained from semi- or non-drying oils such as castor oil and lesquerella oil. The preferred $R_{10}$ and $R_{11}$ groups are also hydrogen, and the preferred $R_9$ may be either hydrogen or methyl.

In still another aspect, the invention provides a process for the preparation of novel monomers Ia using precursor hydroxy long-chain compounds. The preparation involves an esterification reaction of a suitable hydroxy long-chain compound with an ethylenically unsaturated carboxylic acid or its derivatives VI to form the corresponding ester Ia. This esterification reaction is identical to the one described above in step (a) of the process for making the waterborne formulations of this invention.

In yet an additional aspect the invention provides another class of novel compounds suitable as internally plasticizing monomers of this invention for forming the novel latex or emulsion compositions described hereinabove. These monomers are substituted ethylenically unsaturated carboxylic acid esters of long-chain olefinic compounds of the formula Ib:

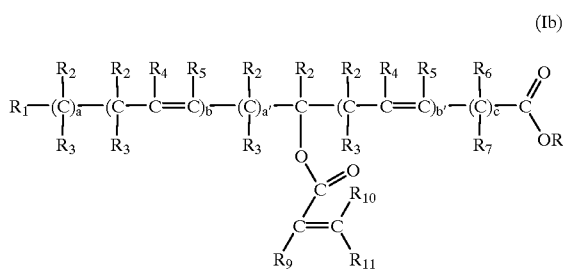
(Ib)

Where $R_1$, $R_2$, $R_3$, $R_4$, $R_5$, $R_6$, $R_7$, $R_9$, $R_{10}$, $R_{11}$, a, a', b, b', and c are as defined above. R is selected from the group consisting of:

phenyl and substituted phenyl;
tolyl and substituted tolyl;
benzyl and substituted benzyl;
alkoxyalkyl group having 1 to 10 carbon atoms;
hydroxyalkyl group having 1 to 10 carbon atoms;
acyloxyalkyl group having 1 to 10 carbon atoms;
a linear or branched alkenyl group having 2 to 10 carbon atoms;

linear or branched alkyl and fluoroalkyl groups having the formula $C_nH_xF_y$, where n is an integer from 2 to 10, x and y are integers from 0 to 2n+1, and the sum of x and y is 2n+1; and a multifunctional moiety having the structure II or III:

(II)

(III)

where $R_{12}$ and $R_{13}$ are the same or different and are independently selected from the group consisting of:
a substituted or unsubstituted, saturated or unsaturated fatty acid chain;
acrylic and substituted acrylic;
a linear or branched alkyl or alkenyl carboxylic acid moiety having 2 to 30 carbon atoms; and
monoalkyl esters of maleic and fumaric acids, where alkyl group contains 1 to 4 carbon atoms The preferred monomers are unsubstituted wherein $R_1$, $R_2$, $R_3$, $R_4$, $R_5$, $R_6$, $R_7$ are hydrogen and are derived from fatty acids obtained from semi- or non-drying oils such as castor oil and lesquerella oil. The preferred $R_{10}$ and $R_{11}$ groups are also hydrogen, and the preferred $R_9$ may be either hydrogen or methyl.

In yet a further aspect the invention provides a process for the preparation of novel monomers Ib using a precursor hydroxy long-chain compounds. The preparation involves an esterification reaction of a suitable hydroxy long-chain compound with an ethylenically unsaturated caroxylic acid or its derivatives VI to form the corresponding ester Ib. This esterification reaction is identical to the one described above in step (a) of the process for making the waterborne formulations of this invention. However, if the starting material Ib contains a hydroxyalkyl group as a substituent on its ester group, i.e., when R=hydroxyalkyl group, the esterification may be carried out either using excess of the acid or its derivative VI to form a monomer containing the diester of ethylenically unsaturated acid VI, or the hydroxy group is suitably protected to form the monoester as described hereinabove.

As mentioned hereinabove, the compositions of this invention have utility in a diverse variety of applications. For instance, the compositions of this invention can be converted to redispersible latex powder by physical drying of the latex composition. The compositions of this invention can also be used to form solvent-free coatings such as adhesives, including pressure sensitive and contact adhesives, which can be used either at ambient or elevated temperatures. The inks or coatings formulations formed from the compositions of this invention may be in the form of waterborne latex or may be in the form of 100% solids. A significant advantage of these compositions is that the coatings, inks, and adhesives formed from these compositions are essentially solvent and VOCs free formulations, thus eliminating environmental pollution yet featuring enhanced properties.

This invention is further illustrated by the following examples which are provided for illustration purposes and in no way limit the scope of the present invention.

EXAMPLES (General)

In the Examples that follow, the following abbreviations are used:

MECO—Methacrylated castor oil
ACO—Acrylated castor oil
MECOME—Methacrylated methyl ricinoleate
ACOME—Acrylated methyl ricinoleate
MELO—Methacrylated lesquerella oil
ALO—Acrylated lesquerella oil
ALOME—Acrylated methyl lesquerolate
$T_g$—Glass transition temperature.
NMR—Nuclear magnetic resonance spectroscopy, usually of either proton, $^1H$; and/or carbon 13, $^{13}C$ nuclei.
IR—Infrared spectroscopy.
DSC—Differential Scanning Calorimetry.
MFT—Minimum film forming temperature.
PVC—Pigment volume concentration.
VOC—Volatile organic content General Analytical Techniques Used for the Characterization: A variety of analytical techniques were used to characterize various starting materials and the compositions of this invention which included the following:

NMR: $^1H$ and $^{13}C$ NMR spectra were recorded on a Bruker AX-200 MHz spectrometer with 5 mm probes at 200 and 50 MHz, respectively.

DSC: A Mettler DSC-30 was used to determine the $T_g$ of the films (mid point value). The heating rate was maintained at 10° C./minute, generally, over a temperature range of −50° C. to 100° C. The flow rate of nitrogen or air is maintained at 20 mL/min.

MFT: MFT of latexes were determined by a MFFT Bar 90 equipment from Byk-Gardner in accordance with ASTM procedure No. D-2354.

Particle Size Determination: Particle size was measured by a Coulter N4 MD sub-micron particle size analyzer.

Tensile Strength Measurements: The tensile strength and percent elongation of the films were determined with a 810 Material Test System according to ASTM D-2370. The specimen were cut to a width of 13 mm, a thickness of 0.06–0.12 mm, and a gauge length of 15 mm. In most cases, the data reported represents an average of 8 measurements.

Measurements of Adhesion and Hardness: The clear latex film adhesion on differing substrates was measured in accordance with ASTM procedure No. D-3359. The latex hardness development was monitored in accordance with ASTM procedure No. D-3363.

Gel Content and Swelling Index: The extent of film cure was determined following the method described in U.S. Pat. No. 4,906,684 with minor modifications. The films that were air-dried for two weeks, and removed from the substrate were tested as follows: (1) About 2 grams samples of films were weighed into glass bottles containing 75 mL of toluene, the bottles were capped and shaken constantly; (2) after 3 days, the bottle contents were decanted onto a weighed fluorocarbon mesh screen (70 micron meter mesh opening), and washed with toluene; (3) the mesh screen was weighed, then dried in a vacuum oven until constant weight was obtained; and (4) after determining the weight of wet gel and dry gel, the gel content and swelling index were determined according to the following equations:

% Gel Content=(weight of dry gel×100)/weight of film

Swelling Index=(weight of wet gel−weight of dry gel)/weight of dry gel

Dry time: The dry time measurements of the film samples of the coatings compositions were measured in accordance with ASTM procedure No. D-1640.

Conical mandrel (⅛") measurements on the film samples were made according to ASTM D-522.

Scrub test was performed in accordance with ASTM procedure No. D-2486.

Sheen and Gloss of the film samples were measured according to ASTM D-523.

Contrast ratio was measured according to D-3022.

Example A

Castor oil was transesterified to methyl ricinoleate using the following procedure: 200 grams of castor oil was refluxed with 300 grams of methanol and 12 grams of sodium methoxide for 1 hour. After removing the solvent in vacuo, the product was extracted using petroleum ether. Upon drying and complete removal of the residual solvent, methyl ricinoleate was formed in quantitative yields.

Example B

Example A was substantially repeated in Example B with the exception that the reaction was carried out using lesquerella oil instead of castor oil as follows. 1000 grams of lesquerella oil was refluxed with 1500 grams of methanol and 60 grams of sodium methoxide for 3 hours. After removing the solvent in vacuo, the product was extracted using petroleum ether. The product was dried and the solvent was removed. Methyl lesquerolate was present in 53–60% mixed with other methyl esters of fatty acids. Purification of methyl lesquerolate from the mixture of methyl esters of fatty acids was performed by vacuum distillation. Several nonhydroxy fractions were distilled at different times in the beginning and the residue in the distillation flask was checked using GC-mass spectroscopy. When the residue contained higher than 93% pure methyl lesquerolate, the distillation was stopped and the product isolated (yield, 550 grams).

Example 1

Castor oil (207 g; 0.627 hydroxy equivalent) was placed in a three-neck flask under a blanket of nitrogen. The entire reaction contents were cooled in an ice bath. Methacryloyl chloride (25.6 g; 0.246 mol equivalent) dissolved in 75 mL of methylene chloride was added slowly to the cooled castor oil with vigorous stirring in about 2 hours. Triethylamine (22.5 g; 0.223 mol equivalent) dissolved in 50 mL of methylene chloride was subsequently added in about an hour. After addition of triethylamine, the solution was allowed to warm to ambient temperature and was stirred for another 4 hours in order to complete the reaction. The precipitated triethylammonium chloride was removed by filtration, and the filtrate was washed with brine solution (saturated NaCl) followed by washings with dil. NaOH and dil. HCl. The organic layer was dried with anhydrous magnesium sulfate and the solvent was removed in vacuo to yield methacrylated castor oil (MECO) in essentially quantitative yields. MECO was stabilized from polymerization by addition of approximately 10 ppm hydroquinone. The structure of the product was verified by $^1H$ and $^{13}C$ NMR spectroscopy.

Example 2

Example 1 was substantially repeated in Example 2 with the exception that the reaction was carried out using acryloyl chloride and castor oil as follows. About 500 grams of castor oil (1.52 mol hydroxy equivalent) was reacted with 149 grams (1.65 mol equivalent) of acryloyl chloride in the presence of 223 grams of triethylamine (2.21 mol equivalent). The reaction was performed using 500 mL of benzene as a solvent. Yield of acrylated castor oil (ACO) was 462 grams. The product was characterized by $^1$H and $^{13}$C NMR spectroscopy.

Example 3

Example 1 was substantially repeated in Example 3 with the exception that the reaction was carried out using methacryloyl chloride and methyl ricinoleate as follows. About 103 grams of methyl ricinoleate (0.312 mol hydroxy equivalent) was reacted with 37 grams (0.356 mol equivalent) of methacryloyl chloride in the presence of 60 grams of triethylamine (0.594 mol equivalent). The reaction was performed using 200 mL of methylene chloride as a solvent. A quantitative yield of methacrylated methyl ricinoleate (MECOME) was obtained and was characterized by $^1$H and $^{13}$C NMR techniques.

Example 4

Example 1 was substantially repeated in Example 4 with the exception that the reaction was carried out using acryloyl chloride and methyl ricinoleate as follows. About 140 grams of methyl ricinoleate (0.424 mol hydroxy equivalent) was reacted with 37 grams (0.36 mol equivalent) of acryloyl chloride in the presence of 60 grams of triethylamine (0.59 mol equivalent). The reaction was performed using 200 mL of methylene chloride as a solvent. A quantitative yield of acrylated methyl ricinoleate (ACOME) was obtained and was characterized by $^1$H and $^{13}$C NMR techniques.

Example 5

Example 1 was substantially repeated in Example 5 with the exception that the reaction was carried out using methacryloyl chloride and lesquerella oil as follows. About 220 grams of lesquerella oil (0.430 mol hydroxy equivalent) was reacted with 24.0 grams (0.230 mol equivalent) of methacryloyl chloride in the presence of 24.2 grams of triethylamine (0.239 mol equivalent) and using 300 mL of methylene chloride as a solvent. A quantitative yield of methacrylated lesquerella oil (MELO) was obtained and was characterized by $^1$H and $^{13}$C NMR techniques.

Example 6

Example 1 was substantially repeated in Example 6 with the exception that the reaction was carried out using acryloyl chloride and lesquerella oil as follows. About 500 grams of lesquerella oil (0.980 mol hydroxy equivalent) was reacted with 97.6 grams (0.1.08 mol equivalent) of acryloyl chloride in the presence of 149 grams of triethylamine (1.48 mol equivalent) and 500 mL of benzene as a solvent. Acrylated lesquerella oil (yield: 519 grams) (ALO) was characterized by $^1$H and $^{13}$C NMR techniques.

Example 7

Example 1 was substantially repeated in Example 7 with the exception that the reaction was carried out using acryloyl chloride and methyl lesquerolate as follows. About 335 grams of methyl lesquerolate (0.900 mol hydroxy equivalent) was reacted with 93.3 grams (83.8 mol equivalent) of acryloyl chloride in the presence of 136.6 grams of triethylamine (1.35 mol equivalent) and 1200 mL of benzene as a solvent. Acrylated methyl lesquerolate (ALOME) (yield, 375.2 grams) was characterized by $^1$H and $^{13}$C NMR techniques.

Example 8

This Example 8 illustrates the preparation of a latex containing the internally plasticizing long-chain olefinic monomer of this invention. To a 1 L reactor kettle equipped with an impeller and charged with 110 grams of deionized (DI) water, which had been deoxygenated (DO) for about half an hour by heating to 80° C. under a nitrogen atmosphere, was added polyvinyl alcohol (80 grams of 10% solution) followed by the addition of 12 grams of Igepal CA-897 (octylphenol ethoxylates with 40 moles of ethylene oxide units obtained from Rhone-Poulenc), 1.2 grams of Igepal CA-630 (octylphenol ethoxylates with 9 moles of ethylene oxide units obtained from Rhone-Poulenc), and 0.6 grams of sodium bicarbonate. The contents were maintained at 80° C. under a blanket of nitrogen, and the preseeding was affected by the addition of ammonium persulfate (0.6 grams) and vinyl acetate (40 grams), and increasing the impeller speed to 200 rpm.

After 15 minutes of preseeding a monomer mixture or pre-emulsion (a stable pre-emulsion can be obtained by mixing all the desirable monomers, surfactants and water over a stir plate for few minutes) consisting of 30 grams of MECOME (from Example 3) and 130 grams of vinyl acetate was added over a period of 3.5 hours at 75° C. maintaining the impeller speed at 200 rpm. Additional amounts of ammonium persulfate (0.6 grams) dissolved in 30 grams of DI water was cofed into the reactor over a period of 3.75 hours. After the addition of all of the monomers and initiators, the contents of the reactor were stirred at 150 rpm for an additional period of 2 hours at 80° C. The cooled latex was filtered from a cheese cloth or a medium mesh filter and poured into a clean container for further evaluation.

The latex exhibited the following properties: particle size: 190 nm; MFT: −1° C.; pH: 4.6; solid contents: 48%; and $T_g$: 18.4° C. (with no driers added). The film formed from the latex exhibited the following film properties: gel content: 62%; swelling: 20; tensile strength: 330 psi; and elongation: 1260%.

Example 9–10

Example 8 was substantially repeated in Examples 9 and 10 with the exception that the latex was prepared using the following amounts of materials in each of these examples:

|  | Example 9 | Example 10[c] |
| --- | --- | --- |
| 10% Polyvinyl alcohol | 40 grams | 60 grams |
| Igepal CA-897 (Rhone Poulenc) | 12 grams | 12 grams |
| Igepal CA-630 (Rhone Poulenc) | 1.2 grams | 1.2 grams |
| NaHCO$_3$ | 0.8 grams | 0.8 grams |
| DI, DO water | 150 grams | 140 grams |
| Ammonium persulfate | 0.6 grams | 0.2 grams |
| Vinyl acetate - for seeding | 40 grams | — |
| Vinyl acetate - with monomer emulsion | 114 grams | 147 grams |
| MECO[a] | — | 16 grams |
| ACOME[b] | 16 grams | — |
| Butyl acrylate | 30 grams | 34 grams |
| Sipomer WAM II (Rhone Poulenc) | — | 3 grams |
| Ammonium persulfate - initiator feed | 0.6 grams | 0.8 grams |
| DI, DO water - for initiator feed | 30 grams | 30 grams |

[a]from Example 1;
[b]from Example 4;
[c]this latex was chased by adding 0.5 grams of sodium formaldehyde sulfoxylate diluted in 40 grams of water containing 0.4 grams of sodium bicarbonate.

In both examples, the seeding was done at 80° C. for about 10 minutes, and the polymerization itself was conducted at 72° C. The monomers were added during a period of about 3.5 hours at an impeller speed of 200 rpm, along with the initiator cofed for about 3.75 hours, and post polymerized for about 1.5 hours. The latices and the films formed from them exhibited the following properties:

|  | Example 9 | Example 10 |
|---|---|---|
| Particle Size | 180 nm | 190 nm |
| MFT | −1° C. | 2° C. |
| pH | 4.9 | 5.1 |
| Solid content | 45% | 43% |
| $T_g$ | 17 | 22 |
| % Gel Content - of film | 61 | 54 |
| Swelling - of film | 24 | 18 |
| Tensile strength - of film | — | 860 psi |
| Tensile elongation - of film | — | 1060% |

Examples 11–13

These examples illustrate the effect of metal driers on the films after curing. Example 8 was substantially repeated in Examples 11 to 13 with the exception that the latex was prepared using the following amounts of materials in each of these examples:

at an impeller speed of 200 rpm, along with initiator cofed for about 3.75 hours in Example 11, 1.5 hours in Example 12, and 2.5 hours in Example 13; and post polymerized for about 2 hours in Examples 11 and 13, and 0.75 hours in Example 12.

The films were formed in these examples with and without the addition of metal driers. The samples with metal driers contained 0.08 weight percent (based on solids) of cobalt hydro-cure II (obtained from OMG, Inc., Cleveland, Ohio) as a metal drier, 0.5 weight percent (based on solids) DRI-RX (obtained from OMG, Inc., Cleveland, Ohio) as a drier accelerator, and 1 weight percent methyl ethyl ketone peroxide as a free radical initiator. The latices and the films formed from them exhibited the following properties:

|  | Example 11 | Example 12 | Example 13 |
|---|---|---|---|
| Particle Size | 200 nm | 200 nm | 180 nm |
| MFT | 0° C. | 1° C. | 0° C. |
| pH | 4.9 | 4.9 | 4.8 |
| Solid content | 48% | 42% | 50% |
| $T_g$ (with no driers added) | 20 | 19 | 29 |
| $T_g$ (after the addition of driers) | 39 | 27 | 48* |

*$T_g$ of the latex coating

|  | Example 11 | Example 12 | Example 13 |
|---|---|---|---|
| 10% Polyvinyl alcohol | 81 grams | — | — |
| Igepal CA-897 (Rhone Poulenc) | 12.3 grams | — | — |
| Sodium dodecylbenzene sulfonate | — | — | 0.5 grams |
| Abex 40[a] | — | 3.5 grams | — |
| Rhodofac BX-660[b] (Rhone Poulenc) | — | 3.5 grams | — |
| Sipomer BEM[c] (Rhone Poulenc) | — | 1.2 grams | — |
| NaHCO$_3$ | 0.6 grams | 0.6 grams | — |
| DI, DO water | 100 grams | 140 grams | 50 grams |
| Ammonium persulfate | 0.6 grams | 0.2 grams | 0.1 grams |
| Vinyl acetate - for seeding | 40 grams | 10 grams | — |
| Preemulsion monomer mixture: |  |  |  |
| Vinyl acetate - with monomer emulsion | 107 grams | 56 grams | 70 grams |
| Internally plasticizing monomer | ALO[d] | ALO[d] | ALOME[e] |
|  | 50 grams | 8 grams | 7 grams |
| Butyl acrylate | 34 grams | 25 grams | 11.5 grams |
| Veova 10 (Shell) | — | — | 10 grams |
| Sipomer WAM I (Rhone Poulenc) | 1.5 grams | 0.75 grams | 0.6 grams |
| Sipomer WAM II (Rhone Poulenc) | 1.5 grams | 0.75 grams | 0.7 grams |
| Ammonium persulfate - initiator feed | 0.6 grams | 0.4 grams | 0.4 grams |
| Sodium dodecylbenzene sulfonate | — | — | 0.5 grams |
| Igepal CA897 (Rhone Poulenc) | — | — | 3.5 grams |
| Sodium carbonate | — | — | 0.4 grams |
| DI, DO water - for initiator feed | 30 grams | 12 grams | 60 grams |
| Chaser Solution |  |  |  |
| FeSO$_4$ | — | — | 0.01 grams |
| t-Butyl hydroperoxide | — | — | 0.4 grams |
| Sodium formaldehyde sulfoxylate | — | — | 0.3 grams |
| DI water | — | — | 8.5 grams |

[a]an anionic surfactant;
[b]an aromatic phosphate ester with 6 mole of ethylene oxide units;
[c]behenylpolyethoxymethylmethacrylate with 25 mole ethylene oxide units;
[d]from Example 6;
[e]from Example 7.

In all of these examples, the seeding was done at 80° C. for about 10 to 15 minutes, and the polymerization itself was conducted at 72° C. The monomers were added during a period of about 3.5 hours (in about 2 hours in Example 13)

Examples 14–15

Example 8 was substantially repeated in Examples 14 and 15 with the exception that the latex was prepared using the following amounts of materials in each of these examples:

|  | Example 14 | Example 15 |
| --- | --- | --- |
| 10% Polyvinyl alcohol | 20 grams | — |
| Igepal CA-897 (Rhone Poulenc) | 6.3 grams | — |
| Igepal CA-630 (Rhone Poulenc) | 1.2 grams | — |
| Abex 3384 (40% solids) | — | 3 grams |
| Rhodofac 13X660 (80% solids) (Rhone Poulenc) | — | 3 grams |
| Sipomer cops-I (40% solids)[a] (Rhone Poulenc) | — | 18 grams |
| $Na_2CO_3$ | 0.4 grams | 1 grams |
| DI, DO water | 100 grams | 120 grams |
| Ammonium persulfate | 0.1 grams | 0.05 grams |
| Preemulsion monomer mixture: |  |  |
| Styrene - preemulsion addition | 47 grams | — |
| Internally plasticizing monomer | ACOME[b] 10 grams | ACOME[b] 8 grams |
| Methyl methacrylate | — | 40 grams |
| Butyl acrylate | 42 grams | 50 grams |
| Acrylic acid | — | 1.5 grams |
| Sipomer WAM I (Rhone Poulenc) | 0.75 grams | 0.75 grams |
| Sipomer WAM II (Rhone Poulenc) | 0.75 grams | 0.75 grams |
| Igepal CA897 (Rhone Poulenc) | 8 grams | — |
| Sipomer cops (Rhone Poulenc) | — | 18 grams |
| Ammonium persulfate - initiator feed | 0.4 grams | 0.4 grams |
| DI, DO water - for initiator feed | 27 grams | 7 grams |
| Chaser solution |  |  |
| $FeSO_4$ | — | 0.01 grams |
| t-Butyl hydroperoxide | 0.4 grams | 0.1 grams |
| Sodium formaldehyde sulfoxylate | 0.4 grams | 0.3 grams |
| DI water | 9 grams | 9 grams |

[a]sodium 1-allyloxy-2-hydroxypropyl sulfonate, obtained from Rhone Poulenc;
[b]from Example 4.

In both of these examples, the seeding was done at 60° C. for about 10 to 15 minutes, and the polymerization itself was conducted at 60° C. The monomers were added during a period of about 2 hours at an impeller speed of 200 rpm, along with the initiator cofed for about 2.5 hours, and post polymerized for about 1.5 to 2 hours at 80° C. The latices and the films formed from them exhibited the following properties:

|  | Example 14 | Example 15 |
| --- | --- | --- |
| Particle Size | 160 nm | 140 nm |
| MFT | −1° C. | −4° C. |
| pH | 4.9 | 4.3 |
| Solid content | 40% | 52% |
| $T_g$ (with no driers added) | 13 | — |
| $T_g$ (after the addition of drier) | 48* | 49* |

*$T_g$ of the latex coating

Examples 16 and 17

Examples 16 and 17, illustrate the formation of the Mill Base formulations used for the preparation of coatings compositions. Specified amounts of the ingredients given below were added to a Lightnin mixer at a mixing speed of 800 rpm, and mixed further at 3500 rpm for 20 minutes.

| Ingredients | Example 16 | Example 17 |
| --- | --- | --- |
| Tronox CR-800 (Kerr McGee) | 455 grams | 1200 grams |
| Huber 70C (DuPont) | 292.5 grams | — |
| Beaverwhite 325 (ECC) | 260 grams | — |
| Duramite (ECC) | 325 grams | — |
| Natrosol Plus (Aqualon) | 12 grams | 5 grams |
| Kathon LX 1.5% (Rohm & Haas) | 5 grams | 4 grams |
| KTPP (Aldrich) | 6.5 grams | 5 grams |
| Byk 034 (Byk Chemie) | 12 grams | 9 grams |
| Tamol 731 25% (Rohm & Haas) | 39 grams | 30 grams |
| Surfynol 465 (Air Products) | — | 4 grams |
| DI water | 715 grams | 500 grams |

Examples 18 and 19

The Examples 18 and 19 illustrate the formation of coatings compositions using the polymeric latices of this invention. The latices formed in Examples 9 and 10 were used in these Examples to form the vinyl-acrylic latex coatings compositions. The coatings were pigmented at 55% pigment volume concentration PVC) using the Mill Base formulation of Example 16. The ingredients and the respective amounts for forming the coatings compositions are given below. For comparison, a control experiment, "Control A," was also carried out using a commercial vinyl-acrylic latex, which had the following properties: MFT: 10° C.; $T_g$: 18° C.; and particle size: 330 nm. The following coatings compositions were prepared using a Lightnin mixer set at 200 rpm.

| Ingredients | Example 18 | Example 19 | Control A |
| --- | --- | --- | --- |
| Example 16 - Mill Base Formulation | 180 grams | 180 grams | 180 grams |
| DI water | 30 grams | 22 grams | 36 grams |
| $Na_2CO_3$ (20%) | 6 grams | 7 grams | 6 grams |
| Byk 035 (Byk Chemie) | 0.4 grams | 0.4 grams | 0.4 grams |
| Surfynol 465 (Air Products) | 1 gram | 1 gram | 1 gram |
| Latex | Example 9 | Example 10 | Commercial |
| % solids | 45 | 43 | 55 |
| Amount | 87 grams | 92 grams | 71 grams |
| Rompaque OP - 62 LO (36.5%) (Rohm & Haas) | 20 grams | 20 grams | 20 grams |
| Polyphobe 107 (25%) (Union Carbide) | 0.8 grams | 1.2 grams | 1.3 grams |
| Polyphobe 102 (25%) (Union Carbide) | 5 grams | 6 grams | 6.4 grams |
| Butyl cabitol | — | — | 3 grams |
| Propylene glycol | — | — | 7 grams |

The coatings of Example 18, 19, and the Control A exhibited the following properties:

| Coating Properties | Example 18 | Example 19 | Control A |
| --- | --- | --- | --- |
| PVC | 55% | 55% | 55% |
| Volume Solids | 33.6% | 33% | 33.5% |
| Weight Solids | 49.9% | 50% | 49.6% |
| Stormer Viscosity | 99 KU | 100 KU | 105 KU |
| ICI Viscosity | 1.6 poise | 2 poise | 2 poise |
| pH | 9.1 | 9.4 | 8.6 |
| VOC (grams/Liter) | <0.4 | <0.4 | 122 |

Coating films were cast onto Leneta charts, aluminum and steel panels. The dry time for the solventless latex coatings was less than the control, their respective films are significantly harder than those from the Control A or other commercial coatings requireing coalescing aids, and adhesion of the solventless coatings of Examples 18 and 19 were superior to the coalescent containing Control A. The MFTs of the solventless coatings of Example 18 and 19 were similar to those formulated with the assistance of organic coalescing aids. Comparative properties of the films formed from the coating compositions of Examples 18 and 19, and the Control A are given below.

| Film Properties | Example 18 | Example 19 | Control A |
| --- | --- | --- | --- |
| Tensile strength | 853 psi | 884 psi | 596 psi |
| Elongation at break | 8.4% | 8.6% | 26% |
| Wet thickness | 7 mil | 7 mil | 7 mil |
| Volume solids | 33.6% | 33% | 33.5% |
| Dry time | 50 minutes | 40 minutes | 55 minutes |
| MFT | 0° C. | 0° C. | 1° C. |
| Pencil hardness | 4 H | 4 H | 2 H |
| Conical mandrel (⅛") | pass | pass | pass |
| Adhesion on Al | 100% | 100% | 80% |
| Adhesion on steel | 100% | 100% | 80% |
| Scrub test: Initial break | 170 | 160 | 170 |
| Scrub test: Film failure | 240 | 230 | 250 |
| Sheen, 85° | 1.9 | 1.9 | 1.7 |
| Contrast ratio | 95 | 95 | 94 |

Various other coatings compositions at different levels of PVC or solid contents of the latices can be made using the procedures of Examples 18 and 19.

Examples 20 and 21

The Examples 20 and 21 illustrate the formation of solventless coatings compositions containing the styrene-acrylic (Example 14) and all-acrylic latex polymers (Example 15). Examples 18 and 19 were substantially repeated in Examples 20 and 21 with the exception that the Mill Base formulation of Example 17 was used with the latices of Examples 14 and 15. For comparison, two control compositions, Control B and Control C, were also prepared under similar conditions using commercial styrene-acrylic (MFT: 1° C., particle size: 80 nm, and $T_g$: −2° C.) and all-acrylic (MFT: 9° C., particle size: 500 nm, and $T_g$: 14° C.) latices. Specific amounts of the ingredients used for forming the coatings formulations in Examples 20 and 21, and the respective controls are given below:

| Ingredients | Example 20 | Control B | Example 21 | Control A |
| --- | --- | --- | --- | --- |
| Example 17 - Mill Base Formulation | 100 grams | 100 grams | 100 grams | 100 grams |
| DI water | 35 grams | 60 grams | 35 grams | 60 grams |
| Na₂CO₃ (20%) | 8.4 grams | 8 grams | 8.4 grams | 8 grams |
| Byk 035 (Byk Chemie) | 0.4 grams | 0.4 grams | 0.4 grams | 0.4 grams |

-continued

| Ingredients | Example 20 | Control B | Example 21 | Control A |
| --- | --- | --- | --- | --- |
| Surfynol 465 (Air Products) | 1.6 gram | 1.6 gram | 1.6 gram | 1.6 grams |
| Latex | Example 14 | Commercial | Example 15 | Commercial |
| % solids - | 45 | 55 | 45 | 55 |
| Amount | 170 grams | 138 grams | 170 grams | 138 grams |
| Polyphobe 107 (25%) (Union Carbide) | 1 grams | 1.3 grams | 1 grams | 1.3 grams |
| Polyphobe 102 (25%) (Union Carbide) | 7 grams | 11 grams | 7 grams | 11 grams |
| Butyl cabitol | — | 3 grams | — | 3 grams |
| Propylene glycol | — | 7 grams | — | 7 grams |

The coatings of Examples 20, 21, and the Controls B and C exhibited the following properties:

| Coating Properties | Example 20 | Control B | Example 21 | Control C |
| --- | --- | --- | --- | --- |
| PVC | 20% | 20% | 20% | 20% |
| Volume Solids | 33% | 32.6% | 33% | 32.6% |
| Weight Solids | 46.3% | 45.6% | 46.3% | 45.6% |
| Stormer viscosity | 82 KU | 84 KU | 82 KU | 84 KU |
| ICI | 1.2 poise | 1.2 poise | 1.2 poise | 1.2 poise |
| pH | 8.2 | 9.1 | 8.2 | 9.1 |
| VOC (grams/Liter) | <0.43 | 118 | <0.43 | 118 |

The coating films were formed and tested from Examples 20, 21, and the Controls B and C following the procedures of Examples 18 and 19. Comparative properties of the films formed from the coating compositions of Examples 20, 21, and the Controls B and C are given below.

| Film Properties | Example 20 | Control B | Example 21 | Control C |
| --- | --- | --- | --- | --- |
| Wet thickness | 6 mil | 6 mil | 6 mil | — |
| Dry time | 50 minutes | 70 minutes | 55 minutes | 60 minutes |
| MFT | −2° C. | −4° C. | −2° C. | 6° C. |
| Pencil hardness | F | 2B | F | B |
| Conical mandrel (⅛") | pass | pass | pass | pass |
| Adhesion on Al | 80% | 80% | 100% | 80% |
| Adhesion on steel | 80% | 80% | 100% | 80% |
| Gloss, 85 | 89 | 93 | 83 | 82 |
| Gloss, 60 | 72 | 75 | 64 | 65 |
| Gloss, 20° | 26 | 32 | 20 | 19 |
| Contrast ratio | 97.3 | 97.2 | 97.5 | 97 |

Example 22

This Example 22 illustrates the use of the internally plasticizing monomer of this invention directly in an UV curable formulation. An ink formulation was made using the monomer composition of Example 7, ALOME as follows. Specified amounts of the ingredients as given below were blended in a Lightnin mixer at 150 rpm for one hour and then to insure thorough mixing the ingredients were transferred to a ball mill and ground to a Hegman #7.

| Ingredients | Parts by weight |
|---|---|
| ALOME, from Example 7 | 21.4 |
| Fluorescent rocket red AX-135 (Day Glo Color) | 1.0 |
| Photomer 3016 (Henkel) | 17.0 |
| Photomer 4061 (Henkel) | 19.0 |
| Photomer 4094 (Henkel) | 15.6 |
| Photomer 4149 (Henkel) | 4.4 |
| Photomer 4770 (Henkel) | 5.5 |
| Photomer 6008 (Henkel) | 11.2 |
| Byk 065 (Byk Chemie) | 0.4 |
| Byk 358 (Byk Chemie) | 0.3 |
| Byk 325 (Byk Chemie) | 0.3 |
| Irgacure 651 (Ciba) | 2.7 |
| Benzophenone | 1.3 |

A 2 mil thick film was applied onto wood, aluminum, paper and steel panels with a draw bar, and irradiated under a 600 W medium pressure mercury UV lamp for 4 seconds at a distance of approximately 7" with a Fusion UV curing source to a hard, smooth film. Similar formulations and applications can be developed using other specialty monomers described herein.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof

What is claimed is:

1. A compound suitable for forming latex or emulsion coatings comprising an ethylenically unsaturated carboxylic acid ester of a long-chain olefinic moiety derived from a non-drying oil, said ester of the formula:

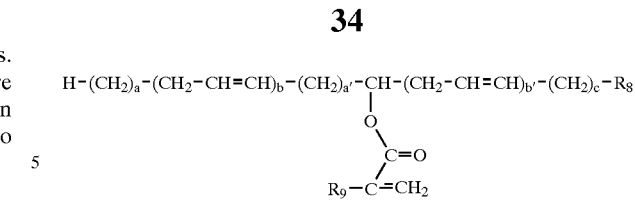

wherein (a) $R_8$ is selected from the group consisting of:
—CN;
—CH$_2$OR;
—CONR'R"; and
—CH$_2$NR'R";
where R, R', and R" are the same or different and are independently selected from the group consisting of:
hydrogen, phenyl, substituted phenyl, tolyl, substituted tolyl, benzyl, substituted benzyl;
alkoxyalkyl group having 1 to 10 carbon atoms;
hydroxyalkyl group having 1 to 10 carbon atoms;
acyloxyalkyl group having 1 to 10 carbon atoms;
a linear or branched alkenyl group having 2 to 10 carbon atoms; and
linear or branched alkyl and fluoroalkyl groups having the formula $C_nH_xF_y$, where n is an integer from 1 to 10, x and y are integers from 0 to 2n+1, , and the sum of x and y is 2n+1;
(b) $R_9$ is either hydrogen or methyl; and
(c) a, a', b, b', and c, are integers, where a and a' have a value of from 2 to 4, b and b' have a value of 0 to 2 with the proviso that sum of b and b' is 1 or 2, and c has a value of 5 to 12.

2. A coating formulation comprising a compound as set forth in claim 1.

3. An adhesive formulation comprising a compound as set forth in claim 1.

4. An ink formulation comprising a compound as set forth in claim 1.

* * * * *